US010543031B2

(12) United States Patent
Vogt et al.

(10) Patent No.: US 10,543,031 B2
(45) Date of Patent: Jan. 28, 2020

(54) BONE CEMENT APPLICATOR WITH THREE-WAY VALVE FOR PRESSURE RELIEF

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 279 days.

(21) Appl. No.: 15/656,369

(22) Filed: Jul. 21, 2017

(65) Prior Publication Data
US 2018/0021075 A1 Jan. 25, 2018

(30) Foreign Application Priority Data

Jul. 21, 2016 (DE) .................. 10 2016 113 467

(51) Int. Cl.
*A61B 17/88* (2006.01)
*B65D 83/00* (2006.01)
(Continued)

(52) U.S. Cl.
CPC ...... *A61B 17/8822* (2013.01); *A61B 17/8816* (2013.01); *A61B 17/8825* (2013.01);
(Continued)

(58) Field of Classification Search
CPC . A61B 17/88; A61B 17/8822; A61B 17/8833; A61B 17/8816; A61B 17/8825; A61B 17/8827; A61L 27/16; A61L 27/50
See application file for complete search history.

(56) References Cited

U.S. PATENT DOCUMENTS 2,446,501 A  8/1948  Weber
6,676,663 B2  1/2004  Higueras et al.
(Continued)

FOREIGN PATENT DOCUMENTS

CN  103418263 A  12/2013
CN  105436047 A  3/2016
(Continued)

OTHER PUBLICATIONS

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.
(Continued)

*Primary Examiner* — Christopher J Beccia
(74) *Attorney, Agent, or Firm* — Norris McLaughlin, P.A.

(57) ABSTRACT

Bone cement applicators and methods apply a bone cement dough in the region of the spine. The applicators and method have at least one tubular cartridge with an internal space, containing starting components of the bone cement, at least one dispensing plunger that is mobile in longitudinal direction on the inside of the at least one cartridge, a hose, an application opening through which the bone cement dough is applicable, a three-way valve being arranged in the hose or on a side of the hose facing the at least one cartridge and in fluid connection with the opening of the at least one cartridge and/or a collecting container arranged on the three-way valve for accommodation of bone cement dough. The three-way valve is appropriately designed and/or arranged in the bone cement applicator such that it, being in a first position, provides a fluid connection between the application opening and the opening of the at least one cartridge and closes a passage to the collecting container and, being in a second position, provides a fluid connection between the application opening and the collecting container
(Continued)

and closes a passage to the opening of the at least one cartridge.

19 Claims, 19 Drawing Sheets

(51) Int. Cl.
    *B01F 13/04*     (2006.01)
    *B05C 17/005*     (2006.01)
    *B05C 17/01*     (2006.01)
    *B65D 81/32*     (2006.01)
    *B01F 5/06*     (2006.01)
    *A61L 27/16*     (2006.01)
    *A61L 27/50*     (2006.01)
    *B01F 3/10*     (2006.01)
    *B01F 13/00*     (2006.01)
    *B01F 13/10*     (2006.01)
    *B01F 15/00*     (2006.01)
    *B01F 15/02*     (2006.01)

(52) U.S. Cl.
    CPC ...... *A61B 17/8827* (2013.01); *A61B 17/8833* (2013.01); *A61L 27/16* (2013.01); *A61L 27/50* (2013.01); *B01F 3/10* (2013.01); *B01F 5/0602* (2013.01); *B01F 5/0615* (2013.01); *B01F 13/0023* (2013.01); *B01F 13/042* (2013.01); *B01F 13/1013* (2013.01); *B01F 15/0087* (2013.01); *B01F 15/0224* (2013.01); *B01F 15/0237* (2013.01); *B01F 15/0292* (2013.01); *B05C 17/00553* (2013.01); *B05C 17/00576* (2013.01); *B05C 17/00583* (2013.01); *B05C 17/0106* (2013.01); *B65D 81/325* (2013.01); *B65D 83/0005* (2013.01); *B65D 83/0072* (2013.01); *A61B 2017/8838* (2013.01); *A61L 2400/06* (2013.01)

(56) References Cited

U.S. PATENT DOCUMENTS

| | | |
|---|---|---|
| 6,935,541 B1 | 8/2005 | Campbell et al. |
| 7,008,433 B2 | 3/2006 | Voellmicke et al. |
| 7,112,205 B2 | 9/2006 | Carrison |
| 7,524,103 B2 * | 4/2009 | McGill .............. A61B 17/8805 366/189 |
| 7,793,800 B2 | 9/2010 | Griesbaum et al. |
| 8,038,682 B2 | 10/2011 | McGill et al. |
| 8,308,731 B2 | 11/2012 | Valale |
| 8,348,494 B2 | 1/2013 | Melsheimer et al. |
| 8,544,683 B2 | 10/2013 | Springhorn et al. |
| 8,992,071 B2 | 3/2015 | Vogt |
| 9,005,209 B2 | 4/2015 | Click et al. |
| 10,258,399 B2 | 4/2019 | Vogt et al. |
| 2004/0074927 A1 | 4/2004 | Lafond |
| 2005/0105384 A1 | 5/2005 | Eder et al. |
| 2007/0162042 A1 | 7/2007 | Dunker et al. |
| 2008/0086143 A1 | 4/2008 | Seaton, Jr. et al. |
| 2008/0188858 A1 | 8/2008 | Luzzi et al. |
| 2008/0319445 A9 * | 12/2008 | McGill .............. A61B 17/8822 606/92 |
| 2009/0105144 A1 | 4/2009 | Vogt et al. |
| 2009/0105366 A1 | 4/2009 | Vogt et al. |
| 2010/0262152 A1 | 10/2010 | Shadduck et al. |
| 2012/0071884 A1 * | 3/2012 | Cooper .............. A61B 17/8827 606/93 |
| 2012/0104030 A1 | 5/2012 | Springhorn et al. |
| 2013/0294193 A1 | 11/2013 | Vogt |
| 2015/0073423 A1 | 3/2015 | Hoefer et al. |
| 2016/0082454 A1 | 3/2016 | Vogt et al. |
| 2016/0178074 A1 | 6/2016 | Aoki |
| 2018/0021076 A1 | 1/2018 | Vogt et al. |

FOREIGN PATENT DOCUMENTS

| | | |
|---|---|---|
| DE | 202005010206 U1 | 9/2005 |
| DE | 10 2005 017 599 A1 | 10/2006 |
| DE | 102005045227 A1 | 3/2007 |
| DE | 102007052116 A1 | 4/2009 |
| DE | 102007050762 B3 | 5/2009 |
| DE | 102008030312 A1 | 1/2010 |
| DE | 10 2011 010 763 A1 | 8/2012 |
| DE | 20 2014 102 416 U1 | 6/2014 |
| DE | 10 2013 109 895 A1 | 3/2015 |
| DE | 11 2014 003 555 T5 | 4/2016 |
| EP | 1074231 A1 | 2/2001 |
| EP | 1464292 A1 | 10/2004 |
| EP | 1392450 B1 | 7/2005 |
| EP | 1596736 A1 | 11/2005 |
| EP | 1614403 A1 | 1/2006 |
| EP | 2 447 184 A1 | 5/2012 |
| EP | 3 272 301 A1 | 1/2018 |
| FR | 1468507 A | 2/1967 |
| JP | 2012101217 A | 5/2012 |
| WO | 2005/051212 A1 | 6/2005 |
| WO | 2007/000066 A1 | 1/2007 |
| WO | 2008/038322 A2 | 4/2008 |
| WO | 2008/097855 A2 | 8/2008 |

OTHER PUBLICATIONS

European Office Action corresponds to EP Application No. 1778422.6 dated Aug. 15, 2018.

Translation of Office Action dated Aug. 29, 2019, in connection with Chinese Patent Application No. 201710601631.2.

* cited by examiner

BONE CEMENT APPLICATOR WITH THREE-WAY VALVE FOR PRESSURE RELIEF

This application claims foreign priority benefit under 35 U.S.C. 119 of German Application No. DE 10 2016 113 467.8 filed Jul. 21, 2016.

BRIEF DESCRIPTION OF THE DISCLOSURE

The invention relates to a bone cement applicator for application of a bone cement in the region of the spine, which preferably is also well-suited for storage of the starting components.

The invention also relates to a method for application of a bone cement, in particular of a pasty multicomponent polymethylmethacrylate bone cement dough using said bone cement applicator.

Accordingly, the subject matter of the invention is, in particular, a simple, inexpensively produced bone cement applicator for vertebroplasty with pasty multicomponent polymethylmethacrylate bone cements by means of which high viscosity pasty starting components of the polymethylmethacrylate bone cement can be mixed and dispensed even with manually operated extrusion devices.

Conventional polymethylmethacrylate bone cements (PMMA bone cements) are made from a powdered component and a liquid monomer component (K.-D. Kühn: Knochenzemente für die Endoprothetik: Ein aktueller Vergleich der physikalischen and chemischen Eigenschaften handelsüblicher PMMA-Zemente. Springer-Verlag Berlin Heidelberg New York, 2001). After mixing the cement powder with the liquid monomer component, said polymethylmethacrylate bone cements are applied in their non-cured pasty state in the form of a cement dough. If mixing systems are used with powder-liquid cements, the cement dough is situated in a cartridge. The cement dough is squeezed from said cartridge through the motion of a dispensing plunger. The dispensing plungers usually have a diameter of between 30 mm and 40 mm and thus have a surface area of 7.0 $cm^2$ to 12.5 $cm^2$ on the outside that is engaged by the pestle of the extrusion device during the extrusion process. The motion of the dispensing plunger is effected by manually operated mechanical extrusion devices, which are also called applicators. Said manual extrusion devices usually reach an extrusion force in the range of approximately 1.5 kN to 3.5 N.

Pasty two-component bone cements, such as are known, e.g., from DE 10 2007 050 762 B3, DE 10 2008 030 312 A1, and DE 10 2007 052 116 B4, are a more recent development. In these two-component bone cements, two pasty starting components are stored in two separate cartridges having two separate dispensing plungers. During application, both pastes are pressed from the cartridges into a static mixer through the motion of the dispensing plungers, and are dispensed through a dispensing tube once the mixing took place. If the composition of the pasty starting components is appropriate, an immediately tack-free cement dough that is ready for application is obtained after the two starting components are mixed. Accordingly, there are no waiting times until the cement dough becomes tack-free which were always obligatory with the previous conventional polymethylmethacrylate bone cements. This allows valuable operation theatre time to be saved.

The application of the previous conventional PMMA bone cements, which consist of a liquid monomer component and a separately stored cement powder component as starting components, involves the two starting components being mixed in cementing systems and/or vacuum cementing systems and the cement dough thus formed then being extruded by means of manually operated extrusion devices. These simple mechanical extrusion devices utilise, in particular, clamp rods that are driven by a manually-actuated tilting lever for extrusion. The manually driven extrusion devices are time-proven throughout the world for decades and as such are the current prior art. Said extrusion devices are advantageous in that the medical user has a feel for the penetration resistance of the bone cement dough into the bone structures (cancellous bone) by means of the manual force to be expended.

In the case of high viscosity pasty starting components and the use of cartridges, in which the dispensing plungers have a total surface area in the range of 7.0 $cm^2$ to 12.5 $cm^2$ at the external plunger sides, which are engaged by the pestles of the extrusion devices, these devices are operable manually either not at all or only while expending a very large force. This exertion of a large force is unreasonable for medical users in operating theatres.

From the adhesives and sealant industry, electrically driven extrusion devices are known as well. Said devices can be driven both with rechargeable batteries and batteries or by means of a stationary electrical power supply. Said devices can extrude particularly thick pasty masses since their extrusion force is very large in some cases. However, it is one disadvantage of the use of electrical motors that these motors contain non-ferrous metals and are expensive purchases. Since the operation theatre area needs to be kept sterile, said devices need to be sterilised with much effort or may even need to be replaced. The presence of electrical wiring may impede the mobility of the user in the operation theatre.

Moreover, pneumatic devices have been proposed as well. Said devices require a stationary or mobile compressed air connection (U.S. Pat. No. 2,446,501 A; DE 20 2005 010 206 U1). This necessitates compressed air hoses, which may impede the mobility of the user.

Alternatively, the use of compressed gas cartridges to provide compressed gas is feasible just as well. Devices have been proposed for this purpose, in which the supply of compressed gas is controlled by a valve and, in addition, the flow of the viscous mass is controlled by a second valve (US 2004/0074927 A1 U.S. Pat. No. 6,935,541 B1). In these devices, the gas cartridges are integrated into the devices. These systems, which are connected to compressed air or contain compressed gas cartridges, always necessitate the presence of a compressed gas source in the absence of which the systems cannot be used.

In vertebroplasty, the application of bone cement is monitored in situ by means of an x-ray procedure. Application devices for vertebroplasty usually have a hose inserted in them through the tip of which the bone cement can be applied to allow the user to work outside the range of the x-rays. For this purpose, a trocar or a cannula can be arranged as well on the hose. Said systems are known, for example, from U.S. Pat. Nos. 7,112,205 B2, 8,038,682 B2, 8,308,731 B2, DE 10 2005 045 227 A1, EP 1 074 231 B1, EP 1 596 736 B1, U.S. Pat. No. 9,005,209 B2, and WO 2008/097855 A2.

Alternatively, other set-ups can be used for keeping the user away from the x-rays, such as are described, for example, in documents U.S. Pat. Nos. 6,676,663 B2, 7,008, 433 B2, 8,348,494 B2, EP1 464 292 B1, EP 1 614 403 B1, US 2008/319445 A9, and WO 2008/038322 A2.

A bone cement applicator for vertebroplasty for application of bone cement comprising a hose, a trocar, and a mixer is known from US 2008/0086143 A1. The bone cement applicator comprises two cartridges arranged next to each other, in which the starting components are stored as well. The bone cement applicator is assembled right before use. In bone cement applicators for vertebroplasty of this type, pressure is exerted on the starting components of the bone cement by means of an extrusion device propelling the dispensing plungers in the cartridges, and the pressure is used to expel the starting components from the cartridges and through the hose. In this context, the starting components are usually mixed first in an upstream static mixer. As a result, the parts of the bone cement applicator serving as borders to the bone cement flow (the cartridges, the housing of the mixer, and the hose) are subject to elastic deformation. When the propulsion of the dispensing plunger is stopped, the elastic force of said parts leads to a volume contraction of said parts such that bone cement continues to exit through the application opening of the hose and/or trocar. This may lead to contamination of the operation theatre or of the user with bone cement or an excessive amount of the bone cement is applied inadvertently. Moreover, when the volume flow of the bone cement dough is to be started up again, pressure needs to be established in the bone cement first to make the bone cement exit through the application opening. This, in turn, delays the time point after propulsion of the dispensing plungers from which the bone cement can actually be applied, which is also undesirable. Since the bone cement dough and the starting components are highly viscous, in particular where pasty starting components are used, all these effects are relatively strongly pronounced. This can be counteracted by the use of massive and expensive metallic housing parts. Said parts need to be cleaned after use and need to be sterilised for further use or need to be recycled with much effort.

U.S. Pat. No. 8,544,683 B2 discloses a cartridge system that is suitable for admixing a small amount to a main starting component. The cartridge system has, aside from a cartridge, a second smaller cartridge arranged in it, whereby, along with the propulsion of a dispensing plunger in the larger cartridge, a dispensing plunger in the smaller cartridge is also driven by a joint connecting element. However, the system is not suitable for mixing the viscous pasty starting components of PMMA bone cement.

A coaxial cartridge system containing a special plunger system is described in the patent, EP1 392 450 B1. The cartridge system is used in the construction materials chemical industry for storing and mixing pasty two-component sealant masses. The plunger system disclosed therein has a cylindrical dispensing plunger for the central cartridge and a ring-shaped dispensing plunger for the second, coaxially arranged cartridge. Both dispensing plungers are driven downstream from the sealant surfaces by means of a support element that possesses, on its rear side, multiple contact surfaces for the pestle of the extrusion device. The support element contains arc-shaped blades. Upon the axial action of the pestle of an extrusion device, both dispensing plungers are moved forward in the direction of the cartridge head. In the process, the pasty components contained in the coaxial cartridges are pushed in the direction of the cartridge head. Simultaneously, the two blades cut the wall of the internal coaxial cartridge into two parts. This system is disadvantageous in that it is inevitable that two cutting processes proceed simultaneously. This means, that energy needs to be expended for both cutting processes, which is then not available for the actual propulsion of the two pasty components. Due to the static mixers being arranged in the dispensing tube and the viscosity of the starting components being high, the mixing of pasty starting components for PMMA bone cements requires a very large amount of propulsion energy that cannot be provided manually, without a hazard and with conventional extrusion devices in the case of larger-sized cartridges. Therefore, a loss of propulsion energy due to two cutting processes proceeding in tandem can be problematic, especially in the case of highly viscous pasty components. Moreover, coaxial cartridges are not easy to fill with the viscous pasty main starting component of a PMMA bone cement. Especially if only small amounts of the PMMA bone cement are to be contained therein, the free cross-sections of the external coaxial cartridge for the main starting component become so small that they cannot be filled using conventional procedures.

Patent FR 1 468 507 discloses a cartridge system, in which a tubular storage container is arranged in a cartridge. The storage container is connected to the cartridge in one place on the end of the cartridge. The cartridge has arranged in it a dispensing plunger, which possesses an opening, in which a part of the tubular storage container is arranged, whereby the opening is smaller than the diameter of the tubular storage container. During the forward motion of the dispensing plunger in the direction of the cartridge head, the mass contained in the cartridge is extruded and the mass contained in the tubular container is moved in the direction of the cartridge head by squeezing-out. For the function of squeezing-out, it is important that the tubular storage container is affixed on the end of the cartridge such that the tubular storage container does not move forward in the direction of the cartridge head along with the dispensing plunger during the squeezing-out without the mass contained therein being extruded. It is a disadvantage of the proposed system that necessarily smaller or larger residues of the mass to be extruded remain in the tubular storage container due to the simple squeezing-out at an opening. The tube creases uncontrollably and unpredictably during the squeezing-out and residual material to be squeezed out stays behind in these creases. As a result, the use of this storage system with multicomponent bone cement pastes is not feasible or only conditionally, since the contents of the at least two initiator components that are arranged separately in the first starting component and in the second starting component have to be exactly defined for the curing of the bone cement to be reproducible. Accordingly, any variation of the mixing ratio needs to be prevented as much as possible. Moreover, due to the chemical composition of the starting components, the cartridges with residual starting components need to be discarded with great effort.

Accordingly, it is the object of the invention to overcome the disadvantages of the prior art. In particular, the invention is to provide a simple and inexpensively produced bone cement applicator for vertebroplasty for pasty multicomponent polymethylmethacrylate bone cements and a method for the application of a cement dough with a bone cement applicator for vertebroplasty with a simple design and being inexpensive to produce, whereby the bone cement dough does not continue to flow once the cement flow is stopped. Moreover, it shall be possible to reuse the bone cement applicator as soon as possible after interruption of the flow of bone cement dough. Contamination of the surroundings and of the user with bone cement dough shall be excluded to the extent possible.

The invention is based, in particular, on the object to develop a simple bone cement applicator for a two-component PMMA bone cement (and/or for a two-component PMMA spine cement) for vertebroplasty. It shall be possible to easily manufacture the bone cement applicator from plastic material and thus the bone cement applicator shall be suitable as a product for single use. It shall be possible to extrude the mixed cement dough with a conventional manually-operated extrusion device of the type that is hitherto conventional for use with PMMA bone cements for the cementing of knee and hip TEP (total endoprosthesis of the hip joint). The bone cement applicator is to be designed appropriately such that an immediate emergency stop of the flowing bone cement dough is feasible without contamination of the surgical theatre (operation theatre) by the bone cement dough and/or continued flow of bone cement dough taking place.

Moreover, it shall be feasible to ready the bone cement applicator as a ready-to-use system for single use in simple manner with a minimal number of assembly steps within a few seconds and, connected to manually drivable medical extrusion devices, the bone cement applicator is to generate a homogeneously mixed cement dough immediately after the manual actuation of the extrusion device commences, and the bone cement applicator is to dispense the homogeneously mixed cement dough at the application opening of a hose, if possible also if the flow of the bone cement was interrupted briefly. It shall be feasible to utilise the manually operated extrusion devices used thus far in operation theatres for the conventional polymethylmethacrylate bone cements, which possess one push rod each and/or one pestle each and, if applicable, one plunger cup each, for dispensation of the two-component polymethylmethacrylate bone cement and/or of the bone cement dough by means of the bone cement applicator to be developed. This is to eliminate the need to purchase special extrusion devices for dispensation of pasty two-component polymethylmethacrylate bone cements.

Preferably, the bone cement applicator to be developed shall necessitate no push rods and/or pestles that are connected to each other and are propelled synchronously in order for the entire device not to become significantly more extensive, longer, and larger than the mixing systems that are thus far customary for the conventional powder-liquid polymethylmethacrylate bone cements. Presently, a simple solution is to be found that allows, if at all possible with just one push rod and/or just one pestle and, if applicable, one plunger cup connected thereto, for the propulsion of two or more pasty starting components from the bone cement applicator both synchronously and manually. It shall be feasible to safely store the pasty starting components of the bone cement separately from each other inside the bone cement applicator. For application, it shall be feasible to safely combine both pasty starting components.

It shall also be feasible to fully extrude all of the two starting components from the cartridges such that the mixing ratio of the initiator components can be reproduced in order to provide for reproducible processing properties of the mixed cement dough and mechanical properties of the cured bone cement.

The bone cement applicator shall also allow a small volume of the homogeneously mixed cement dough of approximately 50 mL and/or maximally 80 mL to be dispensed without any substantial residual amounts (more than 20 mL) remaining in the system and needing to be discarded with great effort. More substantial volumes of the cement dough are not desired for preferred applications in vertebroplasty. The low amounts specified above are sufficient for the application in vertebroplasty.

A first specific embodiment of the bone cement applicator shall allow for extrusion and preferably storage of two pastes at a volume ratio of more than or equal to 95 to 5 or preferably more than or equal to 98 to 2. In this context, said first embodiment of the bone cement applicator is intended for those pasty multicomponent polymethylmethacrylate bone cements, in which a low-volume pasty starting component can be mixed very easily with a large-volume pasty starting component, whereby the low-volume pasty starting component dissolves within a few seconds in the large-volume pasty starting component.

Preferably, pasty starting components that can be applied right after the extrusion, i.e. where there is no time required for swelling of the PMMA bone cement, are used as starting components. The bone cement applicator shall be designed appropriately such that any confusion of the relevant assembly steps by the user is excluded to the extent possible by design means and such that the bone cement applicator can be used by largely untrained personnel as well. Moreover, a method for mixing the pasty starting components and for dispensing the homogeneously mixed cement dough shall be provided.

The objects of the invention are met by a bone cement applicator for application of a bone cement dough in the region of the spine, the bone cement applicator comprising
at least one tubular cartridge with an internal space, whereby the internal space of the at least one cartridge contains starting components of the bone cement;
at least one dispensing plunger for expelling the starting components from the at least one cartridge through an opening of the at least one cartridge, whereby the at least one dispensing plunger is mobile in longitudinal direction on the inside of the at least one cartridge;
a hose;
an application opening through which the bone cement dough is applicable;
a three-way valve being operable from outside and being arranged in the hose or on a side of the hose facing the at least one cartridge, whereby the three-way valve is in fluid connection with the opening of the at least one cartridge;
a collecting container arranged on the three-way valve for accommodation of bone cement dough, whereby the three-way valve is appropriately designed and is appropriately arranged in the bone cement applicator such that it, being in a first position, provides a fluid connection between the application opening and the opening of the at least one cartridge and closes a passage to the collecting container and, being in a second position, provides a fluid connection between the application opening and the collecting container and closes a passage to the opening of the at least one cartridge.

It is preferred according to the invention for the bone cement applicator to be designed for vertebroplasty and it can therefore be used and is well-suited for vertebroplasty.

The starting components of the bone cement, in particular of the two-component or multicomponent polymethylmethacrylate bone cement, are preferred to be fluid, particularly preferably to be pasty.

According to the invention, it is preferred for the three-way valve to be operable by hand.

The invention can provide the hose to comprise the application opening, in particular a Luer system adapter or a trocar with the application opening, and/or to comprise a connecting opening that is situated opposite from the application opening.

The application opening is in fluid connection with the hose.

Being on the side of the cartridge shall be understood to mean that the arrangement is situated with respect to the flow direction of the bone cement dough and/or of the starting components with the three-way valve being in the suitable position, meaning on the side from which the bone cement dough and/or the starting components flow in.

The three-way valve is arranged in the hose or on the end of the hose that is situated opposite from the application opening.

The three-way valve or the end of the hose that is situated opposite from the application opening is in fluid connection with the opening of the at least one cartridge.

Preferably, the invention can provide a mixing tube with a mixer to be arranged between the at least one cartridge and the three-way valve or between the at least one cartridge and the end of the hose that is situated opposite from the application opening.

The at least one dispensing plunger of the at least one cartridge is preferably arranged in the end of the at least one cartridge that is situated opposite from the opening of the at least one cartridge.

The invention can provide a mixer for mixing of the bone cement, in particular a static mixer, to be arranged between the opening of the at least one cartridge and the hose or between the opening of the at least one cartridge and the three-way valve, whereby the three-way valve preferably is arranged between the mixer and the hose, whereby the three-way valve, being in the first position, provides a fluid connection between the application opening and the mixer and, being in the second position, closes the passage to the mixer.

As a result, the starting components from the at least one cartridge can be mixed better. In addition, due to the arrangement of the three-way valve according to the invention, the pressure of the bone cement dough in the mixer is maintained and therefore bone cement dough is expellable again through the hose and the application opening right after the three-way valve is opened again without the pressure in the mixer having to be built up again. As a result, the bone cement dough can be provided more rapidly after the three-way valve is opened.

The present invention also proposes that the bone cement applicator is operable by means of a manually operated extrusion device and that the at least one dispensing plunger is movable in the at least one cartridge by manual force, whereby the cross-section of the internal space of the one cartridge is maximally 3.5 cm$^2$, preferably is maximally 2.5 cm$^2$, or the cross-section of all internal spaces of the cartridges taken together is maximally 3.5 cm$^2$, preferably is maximally 2.5 cm$^2$, and/or that the propulsion area of the at least one dispensing plunger is maximally 3.5 cm$^2$, preferably is maximally 2.5 cm$^2$.

The at least one dispensing plunger being movable in the at least one cartridge by manual force shall be understood to mean that the at least one dispensing plunger can be moved in the at least one cartridge by means of a manually driven extrusion device.

Due to the maximum cross-sectional and/or propulsion areas, which limit the force required for expulsion and mixing of the starting components of the bone cement, being as specified above, the viscous bone cement dough can be expelled from the at least one cartridge through the hose and, if applicable, through the mixer by manual force. As a result, a manually driven and/or drivable bone cement applicator can be provided that works without having a connection for an external energy source and without having an internal energy source and therefore is ready for use at all times and independent of the external circumstances, and/or an extrusion device that works without a connection for an external energy source and also without an internal energy source and therefore is ready for use at all times and independent of the external circumstances can be used.

Moreover, the invention can provide at least part of the hose to be flexible and/or the application opening to be arranged in a connection with an internal thread, in particular in a Luer system adapter, or in a trocar.

As a result, the bone cement applicator can also be used in regions that are difficult to access. Moreover, the hose and, if applicable, the trocar, allow the input of bone cement to be monitored with an x-ray procedure without the user of the bone cement applicator being directly exposed to the x-rays. The trocar can be connected to the remainder of the hose by means of an internal thread, in particular by means of a Luer system. Having a Luer system adapter in place makes the bone cement applicator and/or the components thereof universally connectable.

Preferably, the invention can just as well provide the collecting container to be impermeable for the bone cement dough towards the outside, preferably the collecting container to be fluid-tight or fluid-tight and gas-tight, and/or the collecting container to have a volume that is at least as large as half the volume of the hose, preferably is at least as large as the volume of the hose.

As a result, the bone cement dough and its components can be prevented from being pushed outwards and from thus soiling and/or contaminating the surgical theatre or the user.

Moreover, the invention can provide the at least one cartridge to comprise, on its rear side, an attachment element for attachment of an extrusion device.

This enables a stable attachment of the extrusion device to the bone cement applicator.

According to a preferred first embodiment, the present invention proposes a bone cement applicator, comprising
a first tubular cartridge with a first cylindrical internal space, whereby a first starting component of a bone cement is contained in the internal space;
a first dispensing plunger that is arranged in the first internal space of the first cartridge such as to be axially mobile and that is provided for expelling the first starting component from the first cartridge through an opening in a cartridge head of the first cartridge that is opposite from the first dispensing plunger;
a second tubular cartridge that is arranged inside the first tubular cartridge, whereby the second cartridge contains a second starting component of the bone cement and has a second dispensing plunger arranged in it, whereby the second dispensing plunger can be used to expel the second starting component from the second cartridge through an opposite opening of the second cartridge in the region of the cartridge head of the first cartridge;
whereby a pressing device is arranged in the internal space of the first cartridge behind the first dispensing plunger and the second dispensing plunger, as seen from the cartridge head, the pressing device comprising a clamping edge for compressing the second cartridge and being propellable axially, whereby the pressing device is propellable appropriately in the direction of the cartridge head such that the second cartridge is being progressively compressed axially during the motion of the pressing device thereby propelling the first dispensing plunger and the second dispensing plunger in the direction of the cartridge head.

Accordingly, arranging at least one internal second cartridge in a larger external first cartridge, whereby the internal second cartridge [comprises] a pressing device that runs inside the external first cartridge and, in the process, propels the dispensing plungers in the cartridges and compresses the wall of the internal second cartridge and thus pushes it out of the way of the pestle of the extrusion device, allows a bone cement applicator for a two-component and/or multi-component bone cement to be provided by means of which even a small amount of at least one second starting component can be mixed homogeneously and reproducibly with a first main starting component at the desired mixing ratio, and can subsequently be applied. As a result, the bone cement applicator is also suitable for storage of the starting components and, moreover, can be manufactured inexpensively. Despite the inexpensive design, the bone cement applicator is easy to use and can also be used with manually driven extrusion devices. Moreover, the risk of the bone cement applicator getting blocked is low such that a bone cement applicator that is particularly reliable in operation is being provided. Moreover, it has been evident, surprisingly, that by this means a narrow cartridge with just one pressing device as the drive for propelling the dispensing plungers for propulsion of the two starting components can be used by means of which the wall or walls of the at least one internal (second) cartridge can be pushed to the side at the same time. By this means, the force required for mixing and expelling the starting components can be minimised such that an extrusion device that can be driven by manual force can be used in conjunction with the bone cement applicator in order to expel the starting components from the cartridges and mix them with each other. Accordingly, said first embodiment is well-suited for admixing small amounts of a second starting components of the bone cement.

Accordingly, the at least one cartridge is implemented by two cartridges, namely the first and the second cartridge, in this first embodiment according to the invention. Accordingly, the at least one dispensing plunger is implemented by the first and the second dispensing plungers.

Preferably, the internal space of the first (external) cartridge has a cylindrical geometry. The same applies to the internal space of the second (internal) cartridge prior to the deformation of the wall of the second cartridge by the pressing device. The cylindrical shape is the simplest shape by means of which the internal spaces of the cartridges can be implemented. A cylindrical shape shall be understood geometrically to mean the shape of a general cylinder with any footprint, i.e. not just a cylinder with a circular footprint. Accordingly, the limiting internal wall of the internal space can be a cylinder with any footprint and the jacket can be a cylinder with any footprint, i.e. including a non-circular or circular footprint. However, according to the invention, a cylindrical geometry with a rotationally symmetrical and, in particular, circular footprint is preferred for the internal space of the first cartridge, since the same is the easiest to manufacture. The wall of the second cartridge can be attached appropriately to the internal wall of the first cartridge such that a cylindrical symmetry of the second internal space deviates from the circular footprint. The pressing device and the first dispensing plunger can just as well be provided to be one-part or firmly connected to each other.

The first dispensing plunger preferably closes tightly against the internal wall of the first cylindrical internal space and the second dispensing plunger closes tightly against the internal wall of the second cylindrical internal space. In this context, the second cylindrical internal space is not deformed or is deformed only on the rear-side end. Particularly preferably, the first dispensing plunger closes tightly against the external wall of the second cartridge in the area, in which the external wall of the second cartridge limits the internal wall of the first cartridge.

Inventive bone cement applicators according to the first embodiment can provide the second cartridge to touch, by its external wall, against the internal wall of the first cartridge and to be attached to the internal wall of the first cartridge.

The invention can preferably provide the external wall of the second cartridge to be attached to the internal wall of the first cartridge, in the front in the area of the cartridge head and in the rear behind the second dispensing plunger, whereby the external wall of the second cartridge preferably is attached to the internal wall of the first cartridge along the entire length of the second cartridge.

This prevents the second cartridge from moving uncontrolled inside the first cartridge and ensuing leakage of the second cartridge, which is being deformed, from arising. A connection and/or attachment of the second cartridge along the entire length of the second cartridge is particularly well-suited for this purpose. Moreover, this can be manufactured easily as well.

Moreover, the invention can provide the first dispensing plunger and the second dispensing plunger to be propelled parallel with respect to each other during the propulsion of the pressing device, preferably the first dispensing plunger and the second dispensing plunger run at the same level in the direction of the cartridge head.

By this means, uniform mixing of the starting components is attained, whereby the mixing ratio and thus the properties of the bone cement to be mixed is/are consistent.

Moreover, the invention can provide the clamping edge to be inclined with respect to the longitudinal axis of the first cartridge, preferably to be inclined at an angle of at least 40° perpendicular to the longitudinal axis in the direction of the internal wall of the first cartridge, particularly preferably to be inclined at an angle between 40° and 80° perpendicular to the longitudinal axis in the direction of the internal wall of the first cartridge.

As a result, the wall of the second cartridge is deformed over a larger inclined surface area, which simplifies the propulsion and allows the deformation to proceed more uniformly. Concurrently, the deformation is sufficient to uniformly drive the second dispensing plunger on the rear side by means of the deforming wall of the second cartridge.

The first embodiment of the invention also proposes to have the clamping edge squeeze the second cartridge and/or the wall of the second cartridge against the internal wall of the first cartridge when the pressing device is being propelled.

As a result, the wall of the cartridge is pushed as far as possible from the range of action of a trailing pestle of an extrusion device such that the same cannot impede the motion thereof.

Moreover, the invention can provide the clamping edge to cover at least 30% of the surface area of the cross-section of the second cartridge, preferably covers at least 60% of the surface area of the cross-section of the second cartridge.

This attains a sufficient deformation such that the second dispensing plunger can be driven by the deforming wall of the second cartridge. Moreover, the wall of the second cartridge is also pushed sufficiently far away from the range of action of a trailing pestle of an extrusion device such that the same cannot impede the motion thereof.

Moreover, the invention can provide a gap between the pressing device and the internal wall of the first cartridge in the region of the second cartridge, whereby the gap is as wide as or wider than the thickness of the wall of the second cartridge.

As a result, the pressing device can run over the deformed second cartridge without the material of the wall of the second cartridge as such having to be compressed and without a deformation of the first cartridge being required, which would lead to an undesired additional expenditure of force during the propulsion of the pressing device.

The first embodiment further proposes the rear side of the pressing device to be designed as a support surface for a pestle of an extrusion device.

By this means, the pressing device can be driven easily using a conventional extrusion device.

According to a preferred refinement of the first embodiment, the invention proposes the diameter of the internal space of the first cartridge to be smaller than or equal to 35 mm, whereby the diameter of the internal space of the first cartridge preferably is smaller than or equal to 20 mm, and/or the first cartridge to have an internal diameter of at most 35 mm and the second cartridge to have an internal diameter of at most 10 mm, preferably the first cartridge to have an internal diameter of at most 20 mm and the second cartridge to have an internal diameter of at most 5 mm.

Due to the inventive design of the first cartridges and/or of the first and second cartridge, it is feasible to accommodate the often particularly viscous and pasty starting components of the bone cement, in particular with regard to the first starting component, in a single bone cement applicator as storage and mixing system, which can still be extruded by the action of a manual force and which can still be filled using conventional techniques. When the diameters are larger, the action of a manual force is not sufficient or not sufficient without further ado for extruding the viscous pasty starting components of the bone cement from the cartridge and/or cartridges. Accordingly, with the diameters as specified, the advantages of the present invention are particularly evident.

Moreover, the invention can provide the clamping edge, by squeezing the second cartridge, to press the thus deformed wall of the second cartridge against the underside of the second dispensing plunger and to thus push the second dispensing plunger in the direction of the cartridge head while the pressing device is being propelled in the direction of the cartridge head.

As a result, a separate or complex drive for the second dispensing plunger can be foregone. Without the second dispensing plunger, simple squeezing-out of the second starting component from the deforming second cartridge would lead to undesired variations in the composition of the bone cement, since the deformation of the second cartridge is associated with the uncontrolled formation of creases, in which unpredictable residual amounts of the second starting components remain and are not being mixed with the first starting component. In contrast, the propulsion of the second dispensing plunger, which can be sealed against the internal wall of the second cartridge by means of seals and/or wiper lips, is always associated with the entire content of the second cartridge being conveyed and expelled.

Preferred embodiments of the present invention can be characterised in that the at least one cartridge, the at least one dispensing plunger, and the hose and, if applicable, the mixer, are made from plastic material, whereby polyethylene-co-vinylalcohol (EVOH), polybutylene-terephthalate (PBT), polyethylene-terephthalate (PET), and polymethacrylic acid methylester-co-acrylonitrile are preferred as plastic materials.

The design with plastic materials is inexpensive and easy to implement. The preferred plastic materials are particularly well-suited due to their resistance with respect to the chemicals contained in the starting components.

The first embodiment of the present invention proposes the pressing device or the clamping edge to be manufactured from metal and/or plastic material and/or glass fibre-reinforced plastic material, whereby the pressing device or the clamping edge is manufactured from steel, aluminium alloys, zinc alloys, polyamide, glass fibre-reinforced polyamide, polyetherketone, polysulfone or combinations of said materials.

Due to the hardness of said materials and a high resistance to elastic deformations (which can also be attained, in particular, by suitable shaping), sufficient deformation of the second cartridge can be attained without the clamping edge itself deforming too strongly.

Preferred bone cement applicators of the first embodiment can just as well be characterised in that the ratio of the volume of the first cartridge and the volume of the second cartridge is at least 95 to 5, preferably is at least 98 to 2.

By this means, small and/or low amounts of a second component are admixed and thus the advantages of the design according to the invention are utilised particularly well. This is the case, because the bone cement applicator according to the invention is characterised in that even such extreme mixing ratios can still be generated homogeneously.

Moreover, the invention can provide the second cartridge to be squeezed appropriately, when the pressing device is exposed to at least 0.5 kN acting in the direction of the cartridge head, such that the squeezed second cartridge fits through a gap between the clamping edge and the internal wall of the first cartridge.

Preferably, this is attained through the selection of a suitable thickness of the wall of the second cartridge and through the selection of a suitable material for the second cartridge. As a result, the bone cement applicator can be extruded and/or used with the expenditure of a manual force.

Moreover, the invention can provide the ratio of the thickness of the wall of the first cartridge and the thickness of the wall of the second cartridge to be at least 11 to 10, and whereby the ratio of the thickness of the wall of the first cartridge and the thickness of the wall of the second cartridge is at least 2 to 1, particularly preferably is at least 3 to 1.

This applies in case the first and the second cartridge consist of the same material. If the internal second cartridge consists of a material with a lower modulus of elasticity and/or a more easily deformed material, the wall thickness of the second internal cartridge can also be selected to be equal to or even larger than the wall thickness of the external cartridge. By this means, the internal second cartridge can be deformed without the external first cartridge being deformed along with it and thus inhibiting the motion of the pressing device and of the dispensing plungers.

The internal second cartridge can be welded into the first cartridge in the form of a finished part. This is important, in particular, if the two cartridges do not consist of the same material.

A refinement of the first embodiment of the present invention proposes a part of the wall of the first cartridge to form a part of the internal wall of the second cartridge, preferably over the entire length of the second cartridge or over at least 80% of the entire length of the second cartridge, and/or a part of the wall of the first cartridge to limit a part of the second internal space of the second cartridge, preferably over the entire length of the second cartridge or over at least 80% of the entire length of the second cartridge.

By this means, a motion of the second cartridge with respect to the first cartridge is restricted particularly effectively. Moreover, the deformation of the wall of the second cartridge can be pre-defined particularly well by this means.

The invention can provide the thickness of the wall of the first cartridge to be at least 1 mm and the [thickness of] the wall of the second cartridge to be at most 0.5 mm.

By this means only the second cartridge is subject to plastic deformation, whereas the first cartridge is not subject to plastic deformation and is hardly subject to any elastic deformation.

According to the first embodiment, the invention can provide the second cartridge to be plastically deformed and/or plastically deformable by the clamping edge.

Moreover, the invention can provide the first cartridge to comprise, on the exterior on the wall on the side opposite from the cartridge head, an attachment means by means of which the bone cement applicator can be connected to an extrusion device.

According to a refinement of the first embodiment, the invention can provide a third tubular cartridge to be arranged inside the first tubular cartridge, whereby the external wall of the third cartridge touches against the internal wall of the first cartridge and is attached to the internal wall of the first cartridge, whereby the third cartridge contains the second starting component or a third starting component of the multicomponent bone cement and has a third dispensing plunger arranged in it, whereby the second starting component or the third starting component is expellable from the third cartridge, by means of the third dispensing plunger, through an opposite opening in the third cartridge in the region of the cartridge head of the first cartridge, whereby the pressing device is arranged behind the third dispensing plunger as seen from the cartridge head and the pressing device comprises a clamping edge for compressing the third cartridge, whereby the pressing device is propellable appropriately in the direction of the cartridge head such that the third cartridge is progressively compressed axially while the pressing device moves and thus the first dispensing plunger, the second dispensing plunger, and the third dispensing plunger are being propelled in the direction of the cartridge head.

By this means, a further starting component can be mixed into the bone cement dough. The third cartridge being filled with the second starting component is advantageous in that this allows the second starting component to be admixed to the first starting component at different places and thus makes a more homogeneous mixing of the starting components attainable.

Preferably, the third tubular cartridge is arranged on the internal wall of the first cartridge that is opposite from the second cartridge. What this symmetry attains is that the action of the force acts symmetrically on the pressing device due to the deformation of the second and third cartridges. By this means, a more uniform propulsion can be attained. In particular, the risk of the pressing device becoming lodged in the first cartridge is reduced, which reduces at least the requisite force for driving the bone cement applicator, attains a more uniform dispensation of the mixed bone cement dough, and reduces or eliminates the risk of complete blockage of the bone cement applicator.

In this context, the invention can provide the third cartridge and/or the third dispensing plunger to comprise the same features as the second cartridge and/or the second dispensing plunger according to any one of the inventive bone cement applicators having an internal second cartridge.

This applies in particular, with respect to the interaction of the third cartridge and/or of the third dispensing plunger with other components of bone cement applicators according to the invention. This results in the same advantages as with the second so cartridge and/or the second dispensing plunger.

The invention can just as well provide at least one fourth tubular cartridge to be arranged inside the first tubular cartridge, whereby the external wall of the at least one fourth cartridge touches against the internal wall of the first cartridge and is attached to the internal wall of the first cartridge, whereby the at least one fourth cartridge contains the second, the third, a fourth and/or each at least one further starting component of the bone cement and the at least one fourth cartridge has a fourth dispensing plunger each arranged in it, whereby the second, the third, the fourth and/or the respective further starting component is expellable from the at least one fourth cartridge, by means of the fourth dispensing plunger, through an opposite opening in the at least one fourth cartridge in the region of the cartridge head of the first cartridge, whereby the pressing device is arranged behind the fourth dispensing plunger or plungers, as seen from the cartridge head, and the pressing device comprises at least one clamping edge for compressing the at least one fourth cartridge, whereby the pressing device is propellable appropriately in the direction of the cartridge head such that the at least one fourth cartridge is progressively compressed axially while the pressing device moves and thus the first dispensing plunger, the second dispensing plunger, the third dispensing plunger, and the fourth dispensing plunger or plungers are being propelled in the direction of the cartridge head.

Again, the invention can preferably provide that the at least one fourth cartridge and/or the respective fourth dispensing plungers comprise the same features as the second cartridge and/or the second dispensing plunger according to any one of the inventive bone cement applicators having an internal second cartridge.

This applies, in particular, with respect to the interaction of the at least one fourth cartridge and/or of the fourth dispensing plunger or respective fourth dispensing plungers with other components of bone cement applicators according to the invention. The invention can just as well provide the at least one fourth cartridge together with the second and third cartridges to be arranged symmetrically with respect to the axis of the first cartridge in order to attain uniform mixing of all starting components and a uniform action of force on the cartridges and on the pressing device.

According to a preferred second embodiment of the present invention, as an alternative to the first embodiment, the invention proposes a bone cement applicator, comprising a tubular cartridge, whereby the internal space of the cartridge is cylindrical;
a cartridge head that limits an end of the tubular cartridge;
a separating wall in an axial arrangement in the cylindrical internal space of the cartridge, whereby the separating wall is connected to the jacket surface of the cylindrical internal space of the cartridge, and whereby the separating wall subdivides the cylindrical internal space of the cartridge, which is limited by the cartridge head, into two spatially separated hollow spaces, whereby the first hollow space contains a first pasty starting component of the bone cement, and the separate second hollow space contains a second pasty starting component of the bone cement;

two dispensing plungers that are arranged in the two hollow spaces of the cartridge such as to be axially displaceable, whereby the dispensing plungers close off the two hollow spaces on the side of the hollow spaces opposite from the cartridge head;

whereby the dispensing plungers are connected to each other on the rear side opposite from the cartridge head by means of a connecting means, whereby a wedge or cone with a blade on the front side of the wedge or cone facing the cartridge head is arranged on the connecting means such that, upon propulsion of the dispensing plungers in the hollow spaces in the direction of the cartridge head, the blade cuts open the separating wall and the wedge or cone pushes the cut-open parts of the separating wall in the direction of the internal wall of the cartridge.

This allows the starting components to be stored in a single common cartridge with a cylindrical internal space, if the starting components in the cartridge are separated from each other by means of a separating wall that is arranged in the internal space of the cartridge, whereby both dispensing plungers are expellable by means of a common connecting means that cuts open the separating wall and bends open the cut-open parts of the separating wall such that a further motion of a driving pestle of an extrusion device is not impeded. As a result, manually-driven extrusion devices with just one pestle can be used, since the inventive design makes the requisite force sufficient for driving and mixing the starting components and for cutting open and deforming the separating wall, or since the requisite force can be invested fully into those four processes. Therefore, due to the inventive design, the force exerted for propelling the starting components, for mixing the starting components, and for cutting open and separating the separating wall, in toto, is not so large as to make the entire extrusion device too difficult to operate. Preferably, equal amounts or similar amounts of starting components of the bone cement are mixed with each other in the second embodiment.

Accordingly, the at least one cartridge is a single tubular cartridge with a cylindrical internal space in said second embodiment. The at least one dispensing plunger is implemented in said second embodiment by the two dispensing plungers that are intended for expelling the two starting components from the two hollow spaces in the cartridge.

Accordingly, the two parts of the separating wall that is cut open by the blade remain connected to the cartridge. However, a third inventive embodiment can be provided by the invention in that two blades that cut a strip from the separating wall are arranged on the connecting means. Said strip is then preferably pushed in the direction of the internal wall of the cartridge and is thus pushed away from the stroke and/or from the motion of the pestle for propelling the dispensing plungers and/or the connecting means.

Particularly preferably, the wedge or cone in the second embodiment deforms the two cut-open parts of the separating wall. The deformation effects a displacement of the material of the parts of the cut-open separating wall in the direction of the internal wall of the cartridge. It is particularly preferred for the parts of the cut-open parts of the cartridge to be folded in the direction of the internal wall of the cartridge.

It is preferred according to the invention for the wedge or cone to have a diameter of at least 1.5 mm, particularly preferably of at least 3 mm, on the basis opposite from the blade. This ensures that a sufficient contact surface for propelling the connecting means and thus the dispensing plungers is presented to a pestle of an extrusion device.

The two hollow spaces are preferred to be cylindrical also and particularly preferably have a footprint in the shape of a semicircle or in the shape of segments of a circle.

The version of the second embodiment of the bone cement applicator with a separating wall that can be cut open is preferably provided for a 1:1 mixture of the starting components.

The invention can provide the separating wall to be at least half as wide as half of the maximum diameter perpendicular to the axis of the cartridge. Moreover, the invention can provide the separating wall to be a planar surface. The separating wall is to divide the cylindrical internal space of the cartridge in the region of the axis of the internal space of the cartridge into two hollow spaces, particularly preferably is to divide into two hollow spaces of equal size.

An alternative refinement of the second embodiment of the present invention proposes the dispensing plungers to consist of multiple parts that are not connected to each other, preferably of a front part and a rear part that can be connected to each other or can be touched against each other. The front part is then simply pushed forward in the hollow spaces by the rear part. In this context, the connecting means is connected or can be connected to the rear or rear-most parts of the dispensing plungers. For stabilisation of the two dispensing plungers and for stabilisation of the motion of the two dispensing plungers in the hollow spaces, the two dispensing plungers are preferably each designed to be one-part and are firmly connected to the connecting means.

Preferably, the invention can provide the separating wall to subdivide the internal space of the cartridge in liquid-tight manner and thus the hollow spaces to be separated from each other in liquid-tight manner.

This assures that the two starting components can be stored in the bone cement applicator and/or in the cartridge even for an extended period of time. This is to prevent the liquid and very mobile monomer component from leaking into the neighbouring hollow space and reacting with the other starting components.

According to a preferred refinement of the second embodiment, the present invention can provide the separating wall to be connected to the jacket surface of the cylindrical internal space of the cartridge along two connecting lines that limit the jacket surface, whereby the connecting lines preferably are arranged opposite from each other, and particularly preferably the axis of the cartridge is situated in the separating wall.

As a result, the dispensing plungers can be propelled uniformly in the hollow spaces and the separating wall can be cut open uniformly at a constant force.

The invention can just as well provide the side of the wedge or cone facing away from the cartridge head to form a contact surface for a pestle of an extrusion device. For this purpose, the pestle of the extrusion device is preferably oriented in a direction in the surface of the separating wall such that the pressure exerted by the pestle on the blade pushes onto the blade appropriately such that the blade cuts through the separating wall and such that the wedge or cone can be driven through the cut in the separating wall. If at all possible, this shall not be associated with the cone or wedge getting tilted.

Moreover, the invention can just as well provide the hollow spaces to have a semi-circular or circular segment-shaped cross-section and the dispensing plungers to have a matching cross-section such that the dispensing plungers close the hollow spaces in each axial position in the hollow spaces.

This makes feasible a bone cement applicator that is particularly easy and inexpensive to implement.

The invention can just as well provide the dispensing plungers to be situated at an appropriate distance from each other by means of the connecting means such that the gap between the dispensing plungers is smaller than or equal to the thickness of the separating wall.

This ensures that the dispensing plungers run stably in the hollow spaces and that the separating wall can be bent open well by the wedge or cone.

The first embodiment can also provide the thickness of the separating wall to be maximally 1.5 mm, preferably to be maximally 1.0 mm, and/or the thickness of the separating wall to be such that the separating wall can be cut by the blade exposed to the action of a propulsion force of 1 kN and can be bent open by the wedge or cone.

This makes sure that the separating wall, provided it is produced from conventional plastic materials, can be cut open without any problems by manually driven extrusion devices, while the starting components are being extruded from the hollow spaces by the dispensing plungers.

Moreover, according to the invention, the second embodiment can provide the diameter of the internal space of the cartridge to be smaller than or equal to 35 mm, whereby the diameter of the internal space of the cartridge preferably is smaller than or equal to 20 mm.

The second embodiment also proposes, according to the invention, that the cartridge has a one-part design that includes the separating wall arranged in it, preferably that the cartridge and the separating wall are made from plastic material as a one-part injection moulded part.

As a result, the two hollow spaces are separated from each other in tight manner such that even storage of the starting components for an extended period of time is made feasible.

Moreover, the second embodiment can provide the blade to consist of a steel alloy, aluminium alloy, zinc alloy, ceramic material, a polyamide, glass fibre-reinforced polyamide, polyimide, polyamide-co-imide, polyetherketone or polysulfone.

Said materials are well-suited for cutting the separating wall and can be processed inexpensively.

A refinement of the invention proposes the ratio of the internal diameter of the cartridge and the distance of the dispensing plunger from the cartridge head to be smaller than or equal to 1 to 4, whereby the ratio of the internal diameter of the cartridge and the distance of the dispensing plunger from the cartridge head preferably is smaller than or equal to 1 to 10.

In the second embodiment, the dispensing plungers can be used for filling the starting components into the hollow spaces, if they initially touch against the cartridge head. The starting components are pressed into the hollow spaces and, in the process, the dispensing plungers are pushed in the direction of the connecting means and/or of the rear side of the cartridge without undesired inclusions of air remaining inside the hollow spaces that would interfere when the starting components are expelled from the hollow spaces by the dispensing plungers. The invention can provide for snap-in means that connect the dispensing plungers to the connecting means.

The objects underlying the present invention are also met by a method for application of a bone cement, in particular of a pasty multicomponent polymethylmethacrylate bone cement dough, with a bone cement applicator according to the invention, comprising the following steps proceeding in the order given:

a) inserting the bone cement applicator into an extrusion device, whereby the extrusion device comprises an axially propellable pestle for propulsion of the at least one dispensing plunger and/or of the pressing device or of the connecting means in the internal space of the at least one cartridge in the direction of the opening of the at least one cartridge;

b) moving the three-way valve to the first position or the three-way valve being in the first position and extruding the starting components by means of the extrusion device by axial propulsion of a pestle of the extrusion device, whereby the pestle pushes the at least one dispensing plunger in the direction of the opening, by means of which the starting components are mixed to form the bone cement and the bone cement dough is pushed through the hose and out of the application opening;

c) moving the three-way valve to the second position;

d) whereby the three-way valve, in the second position of the three-way valve, stops the flow of the starting components out of the at least one cartridge into the hose and part of the bone cement dough in the hose that is pressurised between the application opening and the three-way valve is pushed through the three-way valve into the collecting container.

In this context, the invention can provide the three-way valve to be moved to the first position again in a step e) after step d) and, by this means, the bone cement dough to be guided again through the three-way valve to the application opening, whereby it is preferred for steps c), d), and e) to be repeated once or multiple times in the order given.

While the three-way valve is closed, i.e. while it is in the second position, it is expedient to stop the propulsion of the pestle and thus the propulsion of the at least one dispensing plunger and to resume these only once the three-way valve is in the open first position again.

Moreover, the invention can provide the method to be implemented with a bone cement applicator according to the first embodiment and can provide, during the extrusion of the starting components in step b), the pressing device to be propelled by the pestle in the direction of a mixing tube, the first dispensing plunger simultaneously being pushed in the direction of the mixing tube by the pressing device, the clamping edge of the pressing device pressing the wall of the second cartridge to the internal wall of the first cartridge, the deformed wall of the second cartridge simultaneously pushing the second dispensing plunger in the second cartridge in the direction of the mixing tube, by means of which the starting components of the bone cement of both cartridges are pushed into the mixing tube, whereby the starting components are mixed in the mixing tube to form a pasty cement dough, and the mixed cement dough flows out of an application opening.

Referring to a first embodiment having a third cartridge, during the propulsion of the pressing device with a pestle in the direction of the dispensing tube in step b), the invention can provide the clamping edge or a further clamping edge of the pressing device to press the wall of the third cartridge to the internal wall of the first cartridge, the deformed wall of the third cartridge to push the third dispensing plunger in the third cartridge in the direction of the mixing tube and, preferably, during propulsion of the pressing device with the pestle in the direction of the mixing tube, the clamping edge or one or more further clamping edge(s) of the pressing device to also press the respective wall of the at least one fourth cartridge to the internal wall of the first cartridge, the deformed wall or the deformed walls of the at least one fourth cartridge to push the respective fourth dispensing plunger in the at least one fourth cartridge in the direction of the mixing tube.

By this means, multiple starting components can be mixed to form a cement dough or a more symmetrical action of force can act on the pressing device such that the pressing device can tilt or be impeded less easily.

Moreover, the invention can provide the extrusion device to be driven manually, by compressed air or by a motor, whereby the manual force, the compressed air or the motor propels the pestle in the direction of the mixing tube.

Manually drivable extrusion devices are preferred according to the invention, since they do not need to be connected to a source of compressed air or an energy source and do not need to contain this kind of source.

Referring to the first embodiment, the invention can provide the pestle of the extrusion device to push onto the side of the pressing device facing away from the dispensing plunger, and the dispensing plungers to be driven by the pressing device.

Alternatively, the invention can provide the method to be implemented with a bone cement applicator according to the second embodiment and, during the extrusion of the starting components in step b), the extrusion of the pasty starting components by means of the extrusion device takes place by axial propulsion of the dispensing plungers with the pestle, whereby the starting components are pushed into the hose, whereby, synchronous with the motion of the dispensing plungers, the separating wall is cut by the blade in the longitudinal direction of the cartridge and the wedge or cone pushes the two cut-open parts of the separating wall in the direction of the internal wall of the cartridge at least sufficiently far outwards such that a further motion of the pestle of the extrusion device is not prevented or impeded by parts of the cut-open separating wall.

A cup can be arranged on the end of the pestle of the extrusion device that faces in the direction of the cartridge, and the cup can be used to push onto the dispensing plungers and/or the connecting means and the wedge or cone in order to propel the dispensing plungers in the cartridge. The cut-open parts of the separating wall then need to be pushed outwards against the internal wall of the cartridge sufficiently far such that they cannot interfere with the motion of the cup.

In methods according to the invention using the second embodiment of the bone cement applicator, the invention can provide the two cut-open parts of the separating wall to remain connected to the internal wall of the cartridge.

This ensures that no loose parts of the cut-open separating wall impede a further motion of the pestle.

The invention can just as well provide the pestle of the extrusion device to push onto the side of the pressing device that faces away from the dispensing plungers, and the dispensing plungers to be driven by the wedge or cone and the connecting means.

As a result, the largest possible fraction of the force made available by the pestle can be used to drive the starting components and to cut and sever the separating wall. This is meant to prevent too much of the force from being applied in an undesired deformation of the cartridge or an interfering tilting of the dispensing plungers.

Moreover, the invention can provide the side of the wedge or cone facing away from the dispensing plungers to comprise a contact surface for contacting the front side of the pestle or of a cup attached to it, whereby the contact surface is equal to or larger than the cross-section of the pestle or the support surface of the cup, whereby, when the pestle is being propelled, the cross-section of the pestle or the support surface of the cup is fully covered by the contact surface or, preferably, the contact surface projects beyond the cross-section of the pestle or the support surface of the cup.

As a result, the motion of the pestle is not impeded by the cut-open parts of the separating wall.

And lastly, the scope of the present invention also proposes the extrusion device to be drivable by hand or by compressed air or electrically.

Manually drivable extrusion devices are preferred according to the invention, since they do not need to be connected to a source of compressed air or an energy source and do not need to contain this kind of source.

The invention is based on the surprising finding, that the pressure acting on the bone cement in the hose can be relieved without any substantial amount of the bone cement continuing to flow out of the application opening by adjusting a three-way valve that is connected to a collecting container, a hose, and at least one cartridge. Simultaneously, this allows the pressure of the bone cement and of the starting components in the cartridge to be maintained all the way to the three-way valve and, in particular, in the mixer, if any is present. As a result, the lapse of time between opening of the three-way valve (after moving it to the first position) to the resumed exit of the bone cement out of the application opening on the tip of the hose is very short. Accordingly, the pressure of the bone cement applicator is maintained between the three-way valve and the at least one dispensing plunger, when the three-way valve is closed (in the second position of the three-way valve), whereas rapid pressure relief of the bone cement applicator is attained between the three-way valve and the application opening since the bone cement flows off through the three-way valve in the second position. To ensure that the bone cement does not contaminate the surroundings or the user, a collecting container is provided that prevents the bone cement dough exiting through the three-way valve from dripping. Preferably, the collecting container is closed for this purpose. Theoretically, it may be sufficient to retain the bone cement dough. The collecting container can just as well be flexible and/or elastic and can expand when it takes up the bone cement exiting from the three-way valve.

The particular advantage of the bone cement applicator according to the invention is that conventional manually-driven extrusion devices that are common for normal PMMA cements can be used to press the two-component spine cement and/or the two-component bone cement for vertebroplasty through a thin hose into the trocar. The augmentation of vertebral bodies takes place under permanent x-ray control. Having a hose between the trocar and the applicator allows the physician to not have to work with his or her hands within the range of the x-rays. No complex expensive hydraulic application devices are required in this context. Moreover, it is advantageous for the bone cement applicator to contain an emergency relief valve in the form of a three-way valve by means of which the extrusion process can be stopped immediately once the cement dough starts to flow into undesired regions of the vertebral bodies. Said emergency relief valve acts as a pressure relief for the application system, in which the trailing pressure of the cement dough from the static mixer is blocked and simultaneously the cement dough situated upstream of the emergency valve is relieved of pressure, by opening a channel leading into the collecting container into which the cement dough can exit until the pressure in the hose and/or in the trocar is relieved. Due to the collecting container, the surgical theatre and/or the gloves of the physician are not contaminated by the bone cement dough exiting at the emergency relief valve.

The first embodiment of the invention is also based on the idea to provide, in a tubular external first cartridge, at least one second smaller internal second cartridge that has a smaller cross-section than the larger external first cartridge, whereby an axially mobile dispensing plunger each is arranged in both cartridges, and to connect the larger dispensing plunger to a pressing device that pushes, by means of a clamping edge, the wall of the at least one smaller internal second cartridge against the wall of the larger first cartridge when the clamping body is moved in the direction of the cartridge head such that the cartridge wall is being deformed and such that the dispensing plunger of the smaller second cartridge is moved by the deformed wall and/or by the progressive deformation of the wall in the direction of the cartridge head during the forward motion of the pressing device. Concurrently, the dispensing plunger of the larger first cartridge is also moved in the direction of the cartridge head during the forward motion. The deformed, squeezed cartridge wall of the internal second cartridge slides through an external lateral opening of the pressing device during the forward motion of the pressing device. During dispensation of the pasty second starting component from the smaller second cartridge by forward motion of the second dispensing plunger, there basically remain no residual amounts of the pasty second starting component in the deformed small second cartridge. It is important in this context that the pressing device possesses, on its rear side, a central support surface for a pestle, whereby the support surface is arranged outside the opening of the pressing device in order to enable an undisturbed extrusion motion of the pestle. Moreover, the invention is based on observing, surprisingly, that highly viscous cement pastes as starting components can be extruded from a cartridge through a static mixer and through a hose by means of manually operated extrusion devices, if the cross-section of the tubular cartridge is equal to or smaller than 35 mm.

The invention of the first embodiment and second embodiment is also based on the idea to use only one cylindrical external cartridge instead of multiple side-by-side cartridges or coaxial cartridges, for separate storage of the two pasty starting components in order to minimise the flow resistance during dispensation. Moreover, it has been evident, surprisingly, that, by this means, a narrow cartridge with just a single dispensing plunger can be used to propel the two starting components. By this means, the force required for mixing and expelling the starting components can be minimised such that an extrusion device that can be driven by manual force can be used in conjunction with the bone cement applicator in order to expel the starting components from the cartridge and mix them with each other and apply them through a hose.

The wall of the internal cartridge(s) being pushed away by means of the pressing device according to the first embodiment allows even small amounts of the PMMA bone cement to be used and allows even small cartridges with internal spaces with small internal diameters to still be extrudable.

In place of two pushing rods and two cups for propulsion of two dispensing plungers, the cylindrical cartridge of the second embodiment is fitted with an axial and axially cuttable separating wall that subdivides the internal space of the cartridge, which is limited by two dispensing plungers and one cartridge head, into two hollow spaces, in which the two pasty starting components can be stored separately. Due to the separating wall being cut and bent open, even small amounts of the PMMA bone cement can be used and even small cartridges with internal spaces with small internal diameters are still extrudable.

Own experiments have shown that a very large pressure drop occurs in the hose, but, in particular, also on a static mixer (if any is present) during the extrusion process of the at least one cartridge due to the high viscosity of the pasty starting components.

Furthermore, the invention is based on observing that highly viscous cement dough can be dispensed from cylindrical cartridges through a static mixer and the hose using commercial, manually driven extrusion devices in an acceptable amount of time and with an application of force that is acceptable since it can be applied manually, if the diameter of the dispensing plunger on its front side is maximally 35 mm or if the diameter of all dispensing plungers on their front side taken together is maximally 35 mm. The design according to the invention provides a bone cement applicator that can realise such small diameters for the application of highly viscous starting components. In this context, the at least one cartridge and/or the hollow spaces of the cartridge can still be filled with the starting components without too much effort.

An exemplary bone cement applicator is composed of
1. a tubular cartridge with an internal diameter that is less than or equal to 20 mm (preferably 15 mm);
2. a separating wall in the longitudinal direction in the cartridge for formation of two separate spaces for storage of a paste A and paste B;
3. a first dispensing plunger for paste A and a second dispensing plunger for paste B;
4. a plunger connecting the two dispensing plungers, whereby the plunger possesses a blade by means of which the separating wall behind the dispensing plungers can be cut open during the forward motion of the plunger;
5. a removable closure on the cartridge head;
6. a mixing tube with a static mixer arranged in it;
7. a three-way valve on the distal end of the mixing tube having a lateral emergency relief opening;
8. a hollow reservoir that is arranged appropriately about the emergency relief valve (three-way valve) such that the emergency relief opening is connected to the hollow space of the reservoir; and
9. a hose that is connected, on one end, to the emergency relief valve and, on the other hose end, to a Luer system adapter.

Pastes A and B form the two starting components of the two-component bone cement in this context.

BRIEF DESCRIPTION OF THE DRAWINGS

Further exemplary embodiments of the invention shall be illustrated in the following on the basis of nineteen schematic figures, though without limiting the scope of the invention. In the figures.

DETAILED DESCRIPTION OF THE DISCLOSURE

For purposes of simplification, the same reference numbers are used for identical components in the figures even if the embodiments are different.

Figure 1:
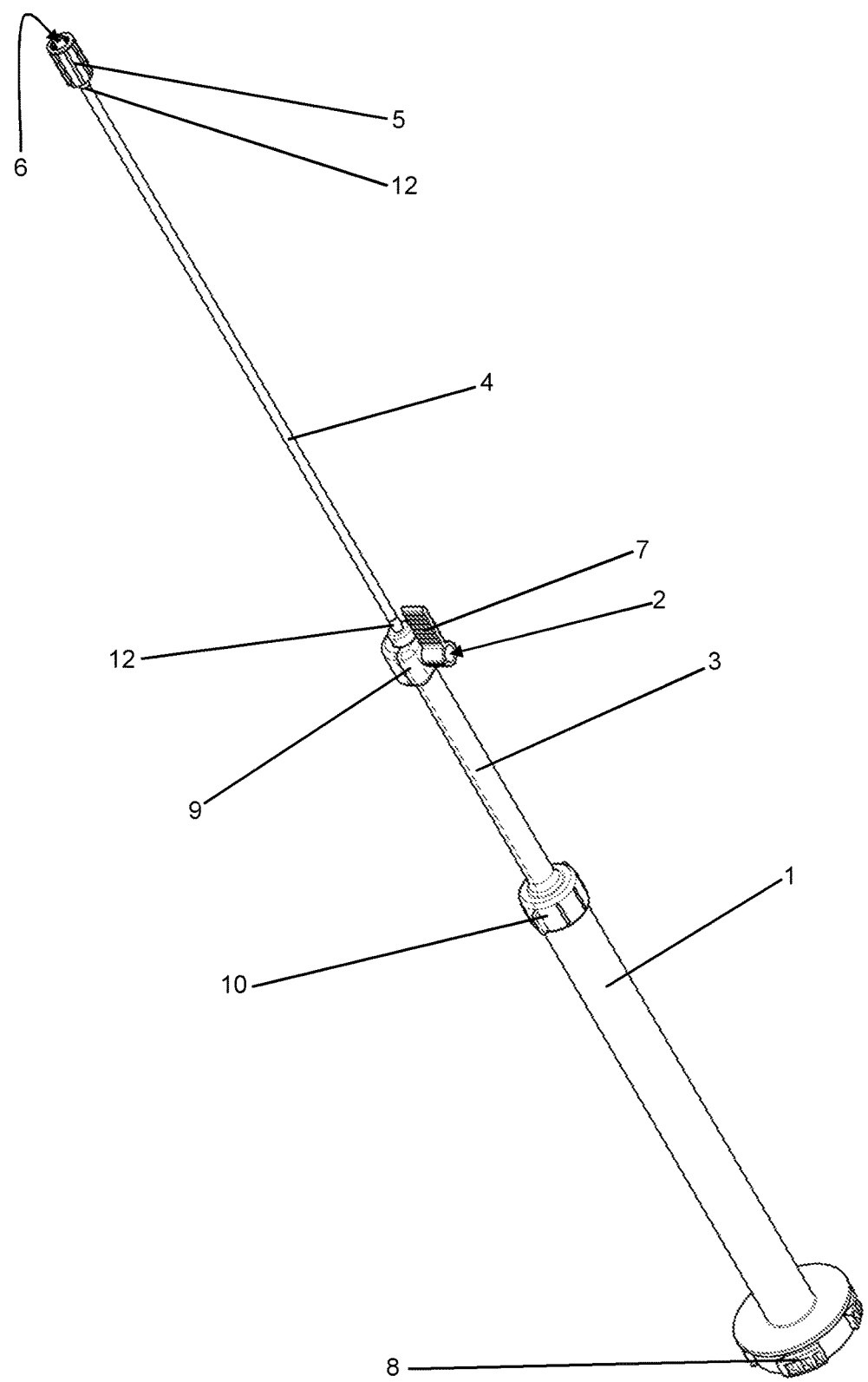
FIG. 1: shows a schematic perspective view of an exemplary bone cement applicator according to the invention.

FIGS. 1 to 6 show an exemplary bone cement applicator for vertebroplasty according to the invention that can have different internal designs in order to implement different embodiments. In this context, FIG. 1 shows a schematic perspective view of an exemplary bone cement applicator according to the invention. Essentially, the bone cement applicator comprises four main parts, namely a cartridge 1, a three-way valve 2, a mixing tube 3, and a hose 4. The starting components of the bone cement to be produced are stored in the cartridge 1. These components are preferably stored separately therein and are stored such that they can be contained therein over extended periods of time with any loss of quality. Seals can be used for this purpose. It is preferred in this context to open the cartridge 1 and to connect it to the other main parts of the bone cement applicator only shortly before use. The two embodiments of the bone cement applicator according to the invention differ in that cartridge 1 has a different internal design.

A Luer system adapter 5, in which an application opening 6 is situated, is arranged on the front side of the hose 4. A trocar (not shown) or a cannula or any other extension with a fitting Luer system connector for application of the bone cement dough in the region of the vertebrae is connectable to said Luer system adapter 5. The trocar (or the other extension) can be considered to be a further part of the bone cement applicator. The application opening 6 is extended correspondingly by these parts, i.e. the application opening 6 is extended to the tip of the trocar by connecting the trocar. Usually, the bone cement applicator is not operated and used in the absence of the trocar.

The three-way valve 2 can be manually operated by means of a T-handle 7 by turning it by 90° and thus transitioning it from a closed position to an opened position or from a closed setting to an opened setting.

The rear side of the cartridge 1 and/or the floor of the cartridge has a connector 8 for connecting an extrusion device (not shown) arranged on it. The extrusion device is to be connected to said connector 8 in order to extrude the content of the cartridge 1, i.e. the bone cement and/or the starting components of the bone cement, from the cartridge 1, then in flow direction through the mixing tube 3, through the (opened) three-way valve 2, and through the hose 4 (and preferably through the trocar) and through the application opening 6 by means of which the bone cement is applied in the vertebra.

A collecting container 9 is arranged in the area of the three-way valve 2 and surrounds the three-way valve 2 axially with respect to the longitudinal axis of the bone cement applicator. The collecting container is plugged together from two plastic parts (see FIGS. 2 and 3).

The cartridge 1 and the mixing tube 3 are connected to each other via an internal thread by means of a union nut 10. For this purpose, an external thread fitting the internal thread of the union nut 10 is provided in the region of the cartridge head that is opposite from the cartridge floor such that the union nut 10 can be screwed onto it by means of the internal thread in order to connect the mixing tube 3 to the cartridge 1. For this purpose, the mixing tube comprises a floor-side enlargement of its circumference in the way of a flange. A seal (not shown in FIGS. 1 to 6) is provided between the mixing tube 3 and the cartridge 1. Before the cartridge 1 is screwed to the mixing tube 3 by means of the union nut 10, the cartridge head of the cartridge 1 can be closed by means of a screwed-on cap (not shown). For this purpose, an internal thread fitting the external thread of the cartridge 1 is provided in the cap.

The three-way valve 2 and the Luer system adapter 5 are connected to the hose 4 in pressure-tight manner by means of a crimp connector using sleeves 12 made of metal. Except for the crimp connector (and except for blades and clamping edges, if any,—refer to the first and second embodiments according to FIGS. 7 to 19), all parts of the bone cement applicator can be made from plastic material, whereby the seals preferably are made from elastic plastic material, such as rubber.

Figure 2:
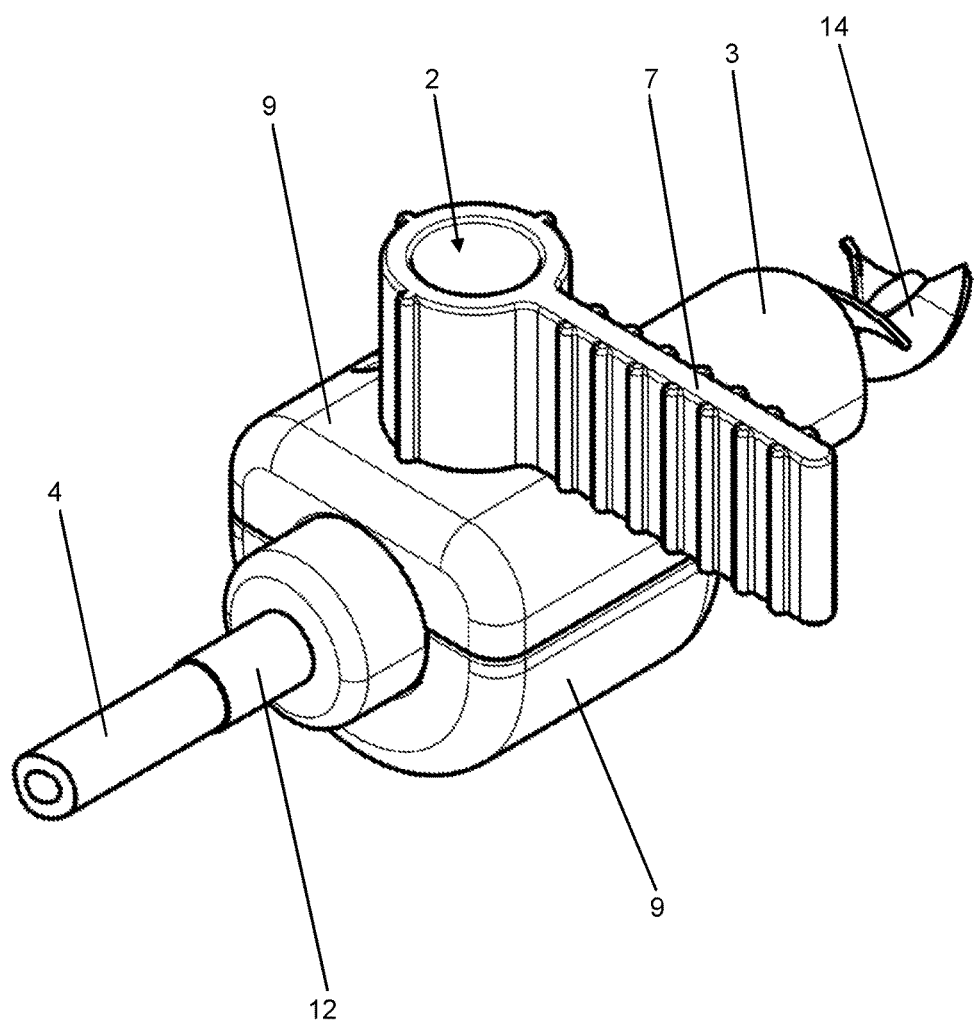
FIG. 2: shows a schematic perspective view of a magnified detail, in which the three-way valve of the bone cement applicator according to FIG. 1 is shown.
Figure 3:
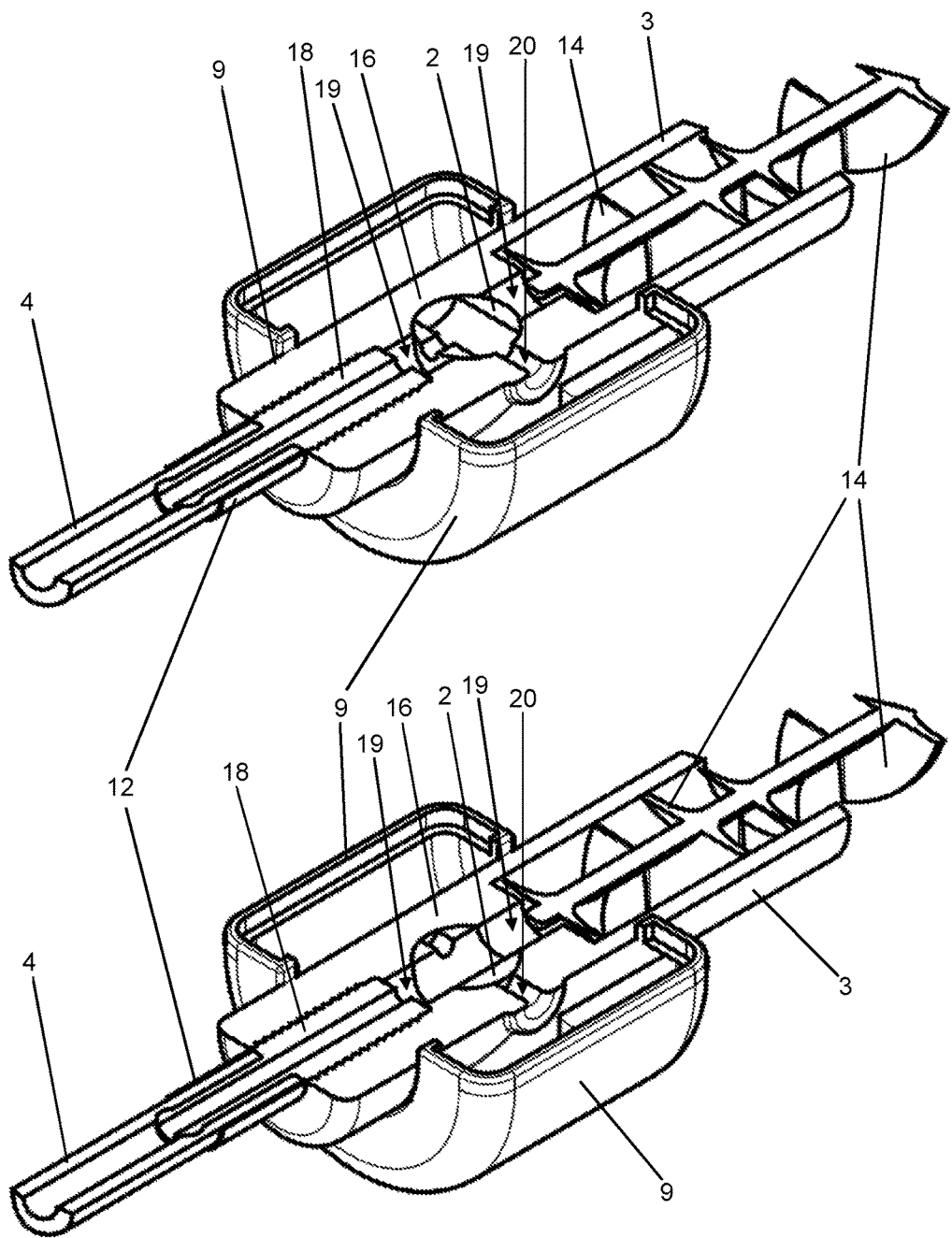
FIG. 3: shows two schematic perspective cross-sectional views through the three-way valve of the bone cement applicator according to FIGS. 1 and 2, namely the three-way valve in closed position (FIG. 3 top) and in open position (FIG. 3 bottom)
Figure 4:
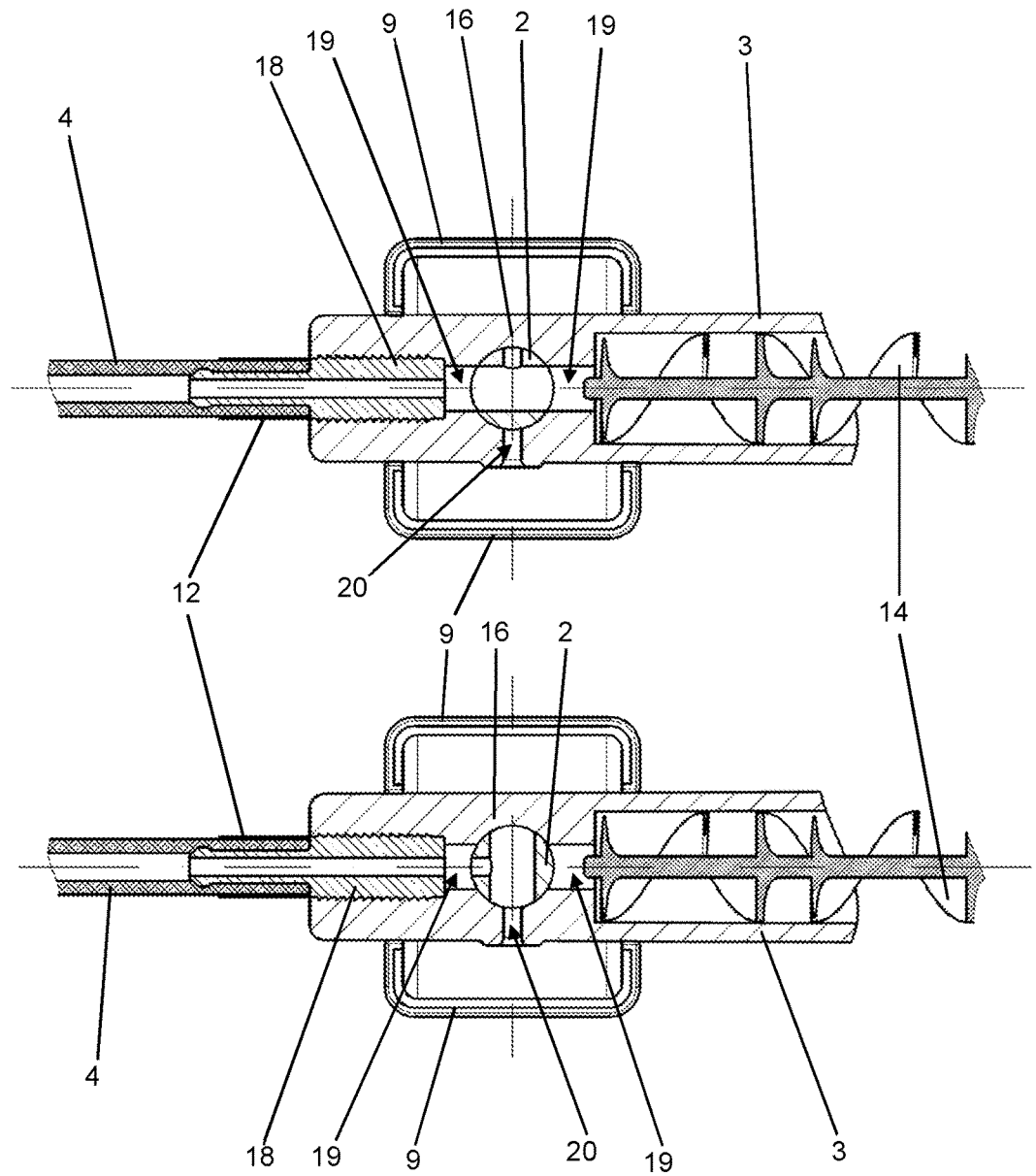
FIG. 4: shows two schematic top views of cross-sectional views through the three-way valve of the bone cement applicator according to FIGS. 1 and 2, namely the three-way valve in open position (FIG. 4 top) and in closed position (FIG. 4 bottom)
Figure 5:
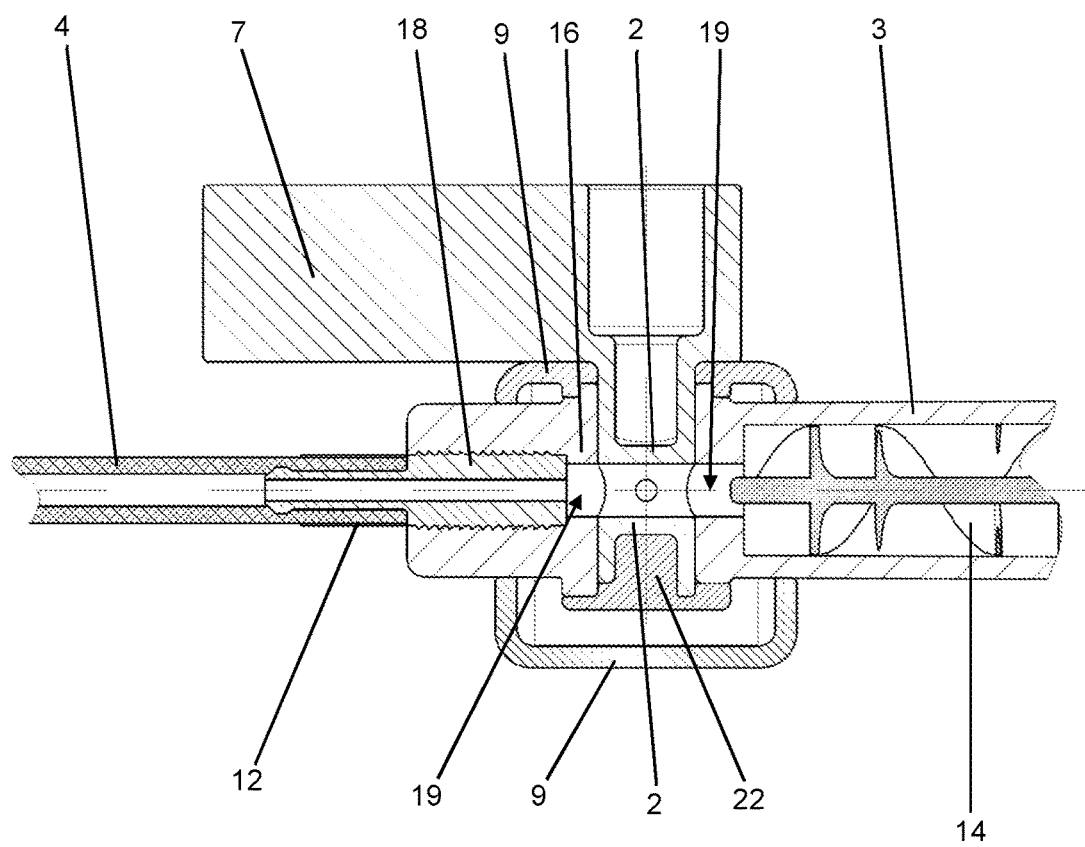
FIG. 5: shows a schematic cross-sectional view of the open three-way valve according to FIGS. 2, 3, and 4 of the bone cement applicator, whereby the sectional plane is selected to be perpendicular to the sectional planes according to FIGS. 3 and 4.

The main part of the bone cement applicator that is essential to the invention is, aside from the cartridge 1, mainly the three-way valve 2 and/or, in particular, the mode of function of the three-way valve 2 together with the collecting container 9 and with the channels formed on the inside of the bone cement applicator. FIG. 2 shows a schematic perspective view of a magnified detail, in which the three-way valve 2 of the bone cement applicator according to FIG. 1 is shown. FIGS. 3 and 4 show cross-sectional views through the three-way valve 2 of the bone cement applicator according to FIGS. 1 and 2, namely the three-way valve 2 in closed position (FIG. 3 top and FIG. 4 bottom) and in open position (FIG. 3 bottom and FIG. 4 top) for illustration of the mode of function of the three-way valve 2 by means of the internal design. Moreover, FIG. 5 shows a schematic cross-sectional view of the open three-way valve according to FIGS. 2, 3, and 4 of the bone cement applicator, whereby the sectional plane is selected to be perpendicular to the sectional planes according to FIGS. 3 and 4.

A static mixer 14 that extends all the way up to the three-way valve 2 is situated on the inside of the mixing tube 3. The static mixer 14 is used to mix the starting components of the bone cement, when these are pressed through the static mixer 14 in the mixing tube 3.

The rotatable three-way valve 2 is sectioned in the plane of symmetry of the channels seen therein in the cross-sectional views according to FIGS. 3 and 4. Accordingly, the channels are cylindrical and continue in the cut-off part of the three-way valve 2 in mirror-symmetrical manner. The channels form a T-part in the three-way valve 2. The three-way valve 2 rests in a fitting valve seat 16 that touches tightly against the three-way valve 2 and thus seals the channels, when these are rotated into the valve seat 16. The valve seat 16 has two passages 19 situated in it by means of which the larger through-going channel in the three-way valve 2 can be connected in fluid-tight manner to the mixing tube 3 on one side and to an insert 18 made of metal for attachment of the hose 4 on the other side.

A feed-through 20 connecting the valve seat 16 to the inside of the collecting container that is closed towards the outside is situated perpendicular to the axis of the two passages 19. The valve seat 16 and the mixing tube 3 are provided as a single part made of plastic material. In the open position of the three-way valve 2 (FIG. 3 bottom, FIG. 4 top, and FIG. 5), the large through-going channel is connected to the two passages 19 and the small perpendicular channel is closed through the valve seat 16. Accordingly, the bone cement can flow from the mixing tube 3 through the three-way valve 2 and the insert 18 into the hose 4. In the closed position of the three-way valve 2 (FIG. 3 top and FIG. 4 bottom), one side of the large through-going channel is connected to the feed-through 20 to the internal space of the collecting container 9 and the small perpendicular channel is connected to the passage 19 to the hose 4, whereas the other passage 19 to the mixing tube 3 is closed by the three-way valve 2. Accordingly, the bone cement can flow from the hose 4 and, if applicable, the trocar connected to the Luer system adapter 5 into the collecting container 9. The pressure for this purpose results from an elastic deformation of the hose 4 and, if applicable, trocar that has built up during the extrusion and/or while the bone cement was pressed through.

Being cylindrical on the outside, the three-way valve 2 is guided through a cylindrical borehole in the valve seat 16 and is connected to a stopper 22 on the side opposite from the T-handle 7 and thus is secured against dropping out or against being inadvertently pulled out of the valve seat 16.

Due to the design according to the invention, it is feasible to rapidly interrupt the flow of bone cement by rotating and thus closing the three-way valve 2 without large amounts of the bone cement continuing to flow through the application opening 6. Simultaneously, leakage of the bone cement and thus contamination of the surroundings or user is prevented by means of the collecting container 9 that takes up any excess of bone cement. Moreover, the pressure in the rear side of the bone cement applicator, i.e. between the three-way valve 2 and the dispensing plunger or dispensing plungers in cartridge 1, is maintained such that the flow of bone cement can be provided again rapidly after the three-way valve 2 is opened again without the pressure having to be built up again in the rear side of the bone cement applicator.

Figure 6:
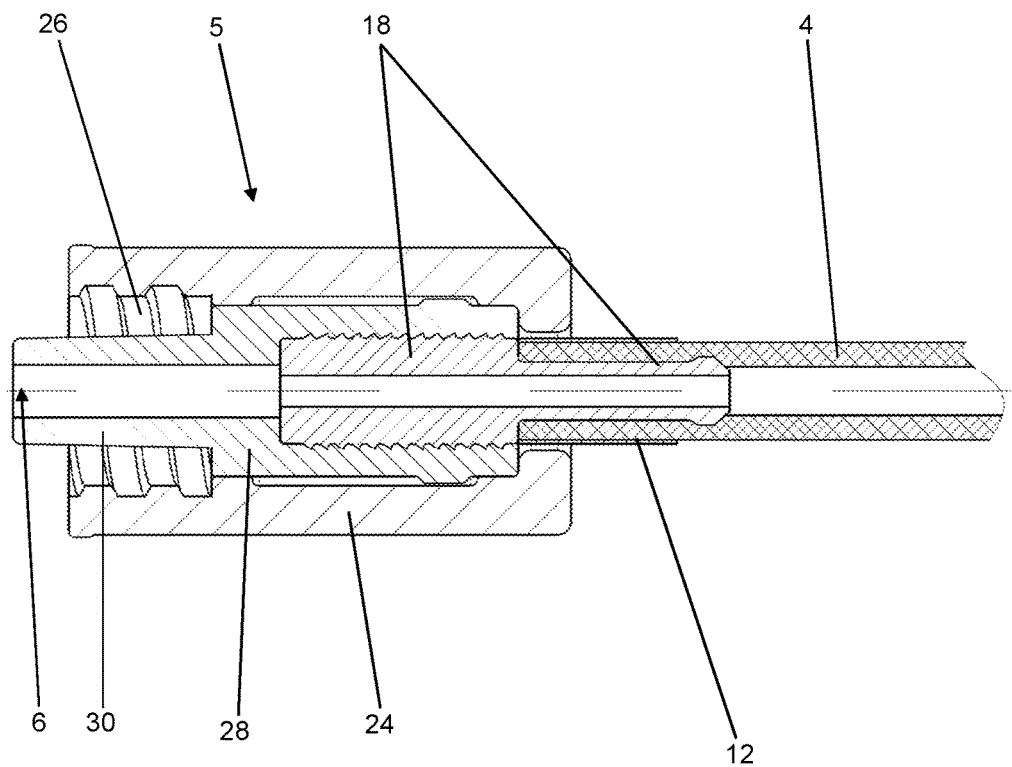
FIG. 6: shows a schematic cross-sectional view of the Luer system adapter on the tip of the bone cement applicator of the magnified detail.

FIG. 6 shows a schematic cross-sectional view of the Luer system adapter 5 on the tip of the bone cement applicator as a magnified detail view. Analogous to the connection of the valve seat 16 to the hose 4, an insert 18 made of a metallic material is situated in the Luer system adapter 5. The hose 4 is crimped to said insert 18 by means of the sleeve 12 in order to produce a pressure-tight connection. In addition, the Luer system adapter 5 consists of an external sleeve 24 with an internal thread 26 and an internal part 28 with a cone 30. A channel that is connected to the hose 4 via a channel of the insert 18 and merges into the application opening 6 on the other side extends inside the internal part 28. The external sleeve 24 and the internal part 28 are produced from plastic material. Theoretically, a different adapter can be provided as well or a trocar or similar component can be firmly connected to the hose 4.

For the viscous bone cement dough to be extrudable with a manually operated extrusion device, i.e. to be extrudable by manual force, the internal diameter of the cartridge 1 must not be too large. Preferably, the internal diameter is less than 35 mm, particularly preferably less than 25 mm. As a result, the resistance caused by the viscous bone cement in the bone cement applicator is not so large that the bone cement can no longer be extruded by manual force by normal users.

Theoretically, the bone cement applicator could be designed easily to include a side-by-side cartridge and could just as well be operated with a motor- or compressed air-driven extrusion device. To be able to use conventional manually-operated extrusion devices having a single centrally-propelled pestle, the cartridge 1 of the bone cement applicator needs to have an appropriate design. The advantage of the three-way valve 2 with the collecting container 9 is, in particular, that said simple manually operated extrusion devices can be used, since the flow of the bone cement can be built up again quickly and/or since the pressure of the bone cement is maintained without requiring many manual strokes with the extrusion device.

Figure 10:
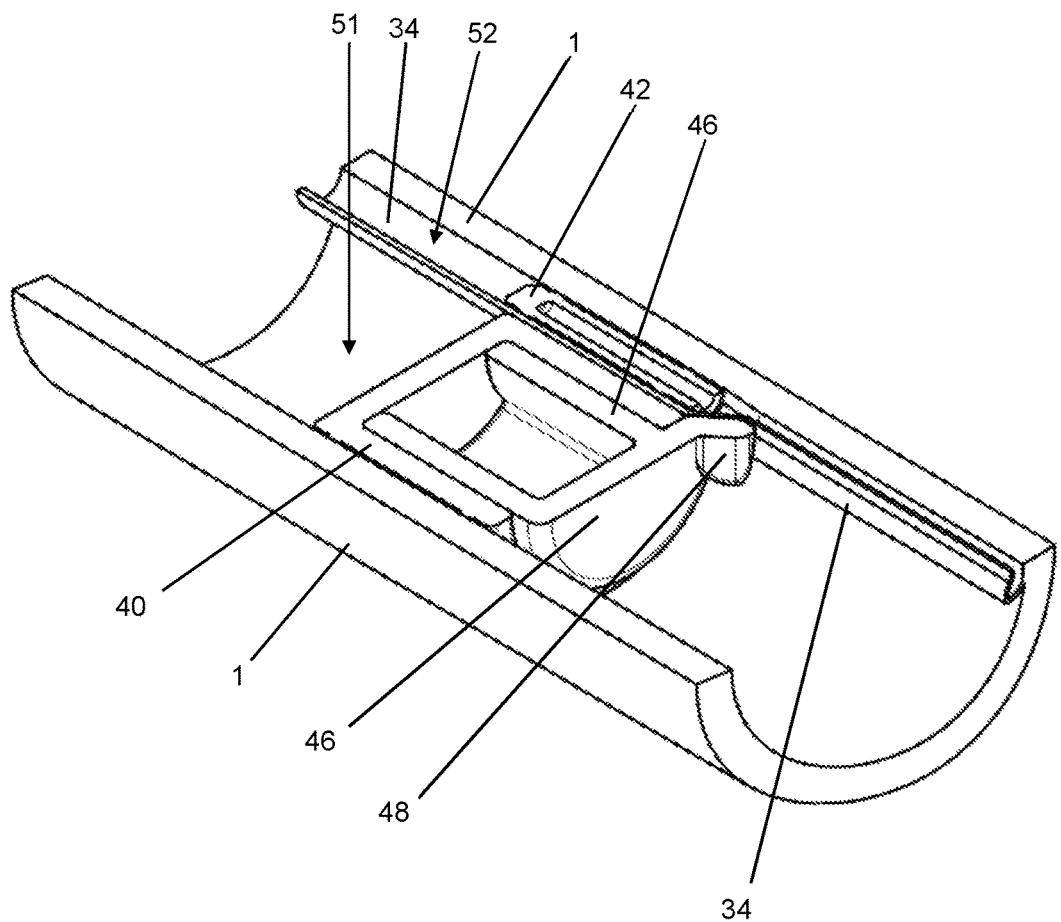
FIG. 10: shows a schematic perspective magnified detail in the form of a cross-sectional view of the motion of the dispensing plungers and of the pressing device in the cartridge of the bone cement applicator according to the first embodiment according to FIGS. 7 to 9.
Figure 11:
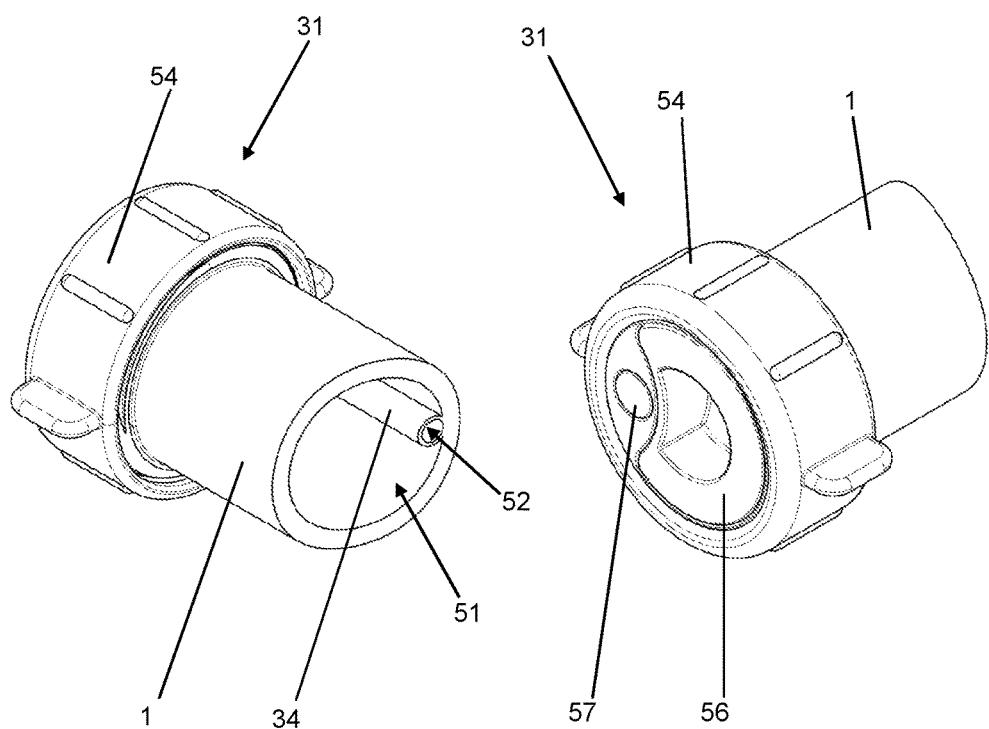
FIG. 11: shows two schematic perspective sectional views of the front region of the cartridge of the first embodiment of the bone cement applicator along with a closure.
Figure 12:
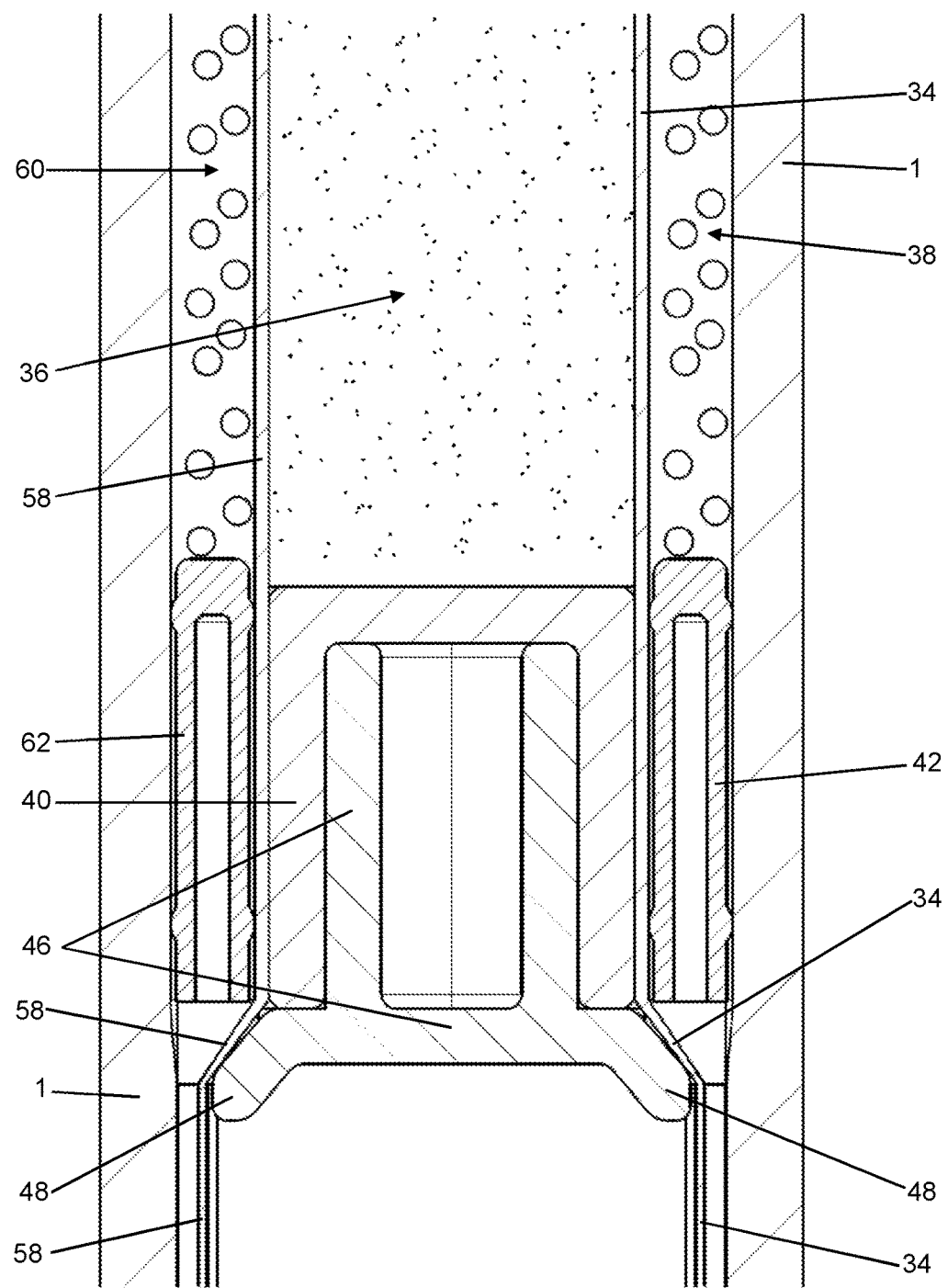
FIG. 12: shows a magnified schematic cross-sectional view of a variant of the first embodiment of the bone cement applicator along with two internal cartridges while the starting components are being expelled.

Two embodiments according to the invention that can be used with a manually-driven extrusion device having a central pestle are proposed in the following. The first embodiment is depicted in FIGS. 7 to 11, whereby an alternative variant of the first embodiment is shown in FIG. 12. The second embodiment is shown in FIGS. 13 to 19.

Figure 7:
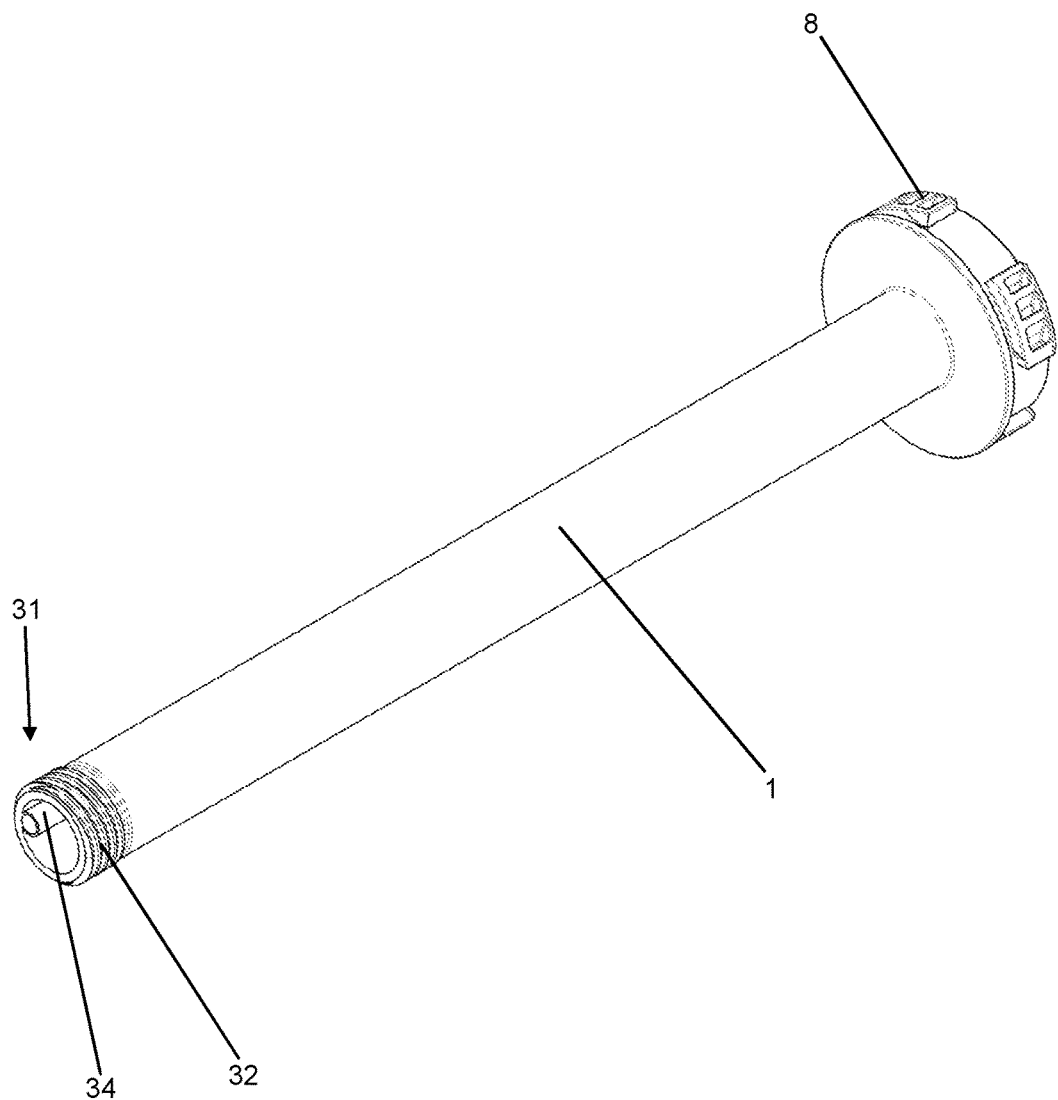
FIG. 7: shows a schematic perspective view of a cartridge having an internal cartridge for implementation of a first embodiment of a bone cement applicator according to the invention.

FIG. 7 shows a schematic perspective view of a cartridge 1 that is designed to include an external cartridge 1 and whose cartridge head 31 has an external thread 32 provided on it. An internal cartridge 34 is arranged in the external cartridge 1. Said cartridge 1, or to be more specific the cartridge system shown, is well-suited for implementation of the first embodiment of a bone cement applicator according to the invention and, in the form shown, can be used as cartridge 1 in the bone cement applicator depicted in FIGS. 1 to 6. FIG. 7 shows a perspective view onto the open cartridge head 31. A closure can be screwed onto the internal thread 32 (see FIG. 11) in order to close the external cartridge 1 and the internal cartridge 34 such that their internal spaces are completely closed.

Figure 8:
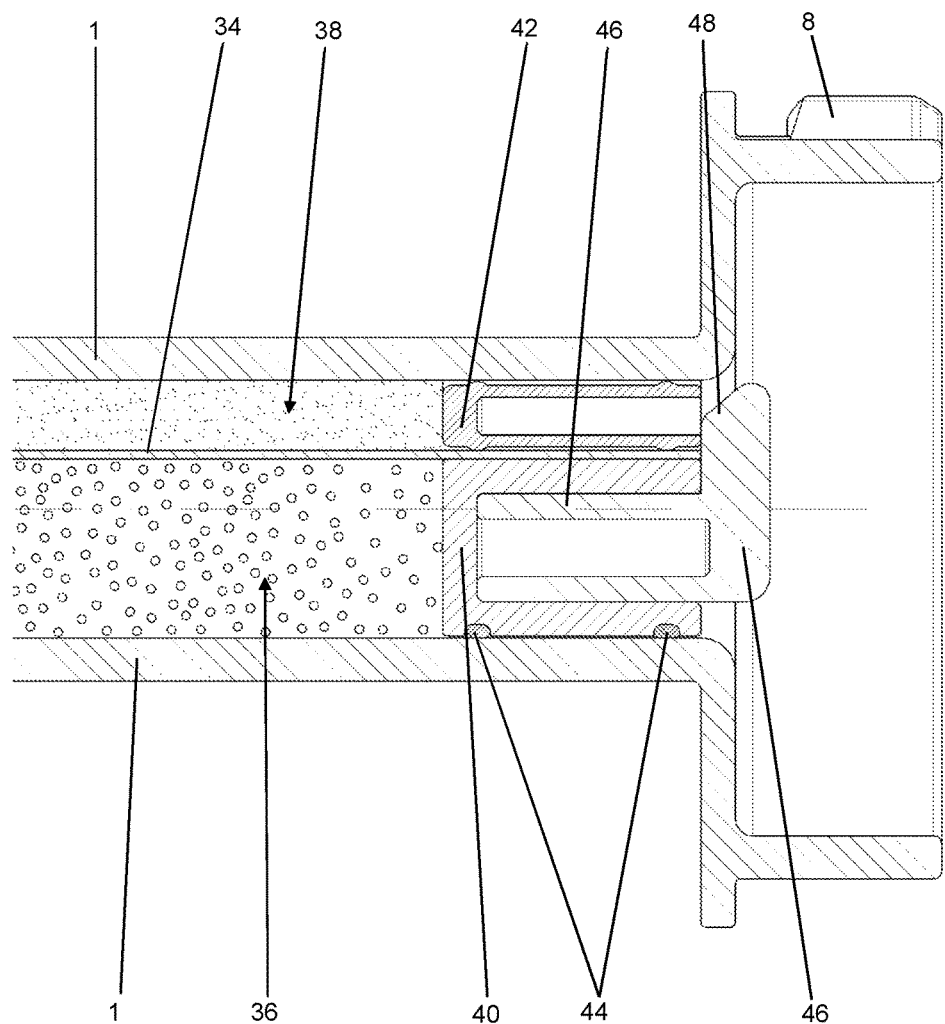
FIG. 8: shows a schematic cross-sectional view in longitudinal direction of the rear side of the cartridge of the first embodiment according to FIG. 7 before the start of the extrusion process.
Figure 9:
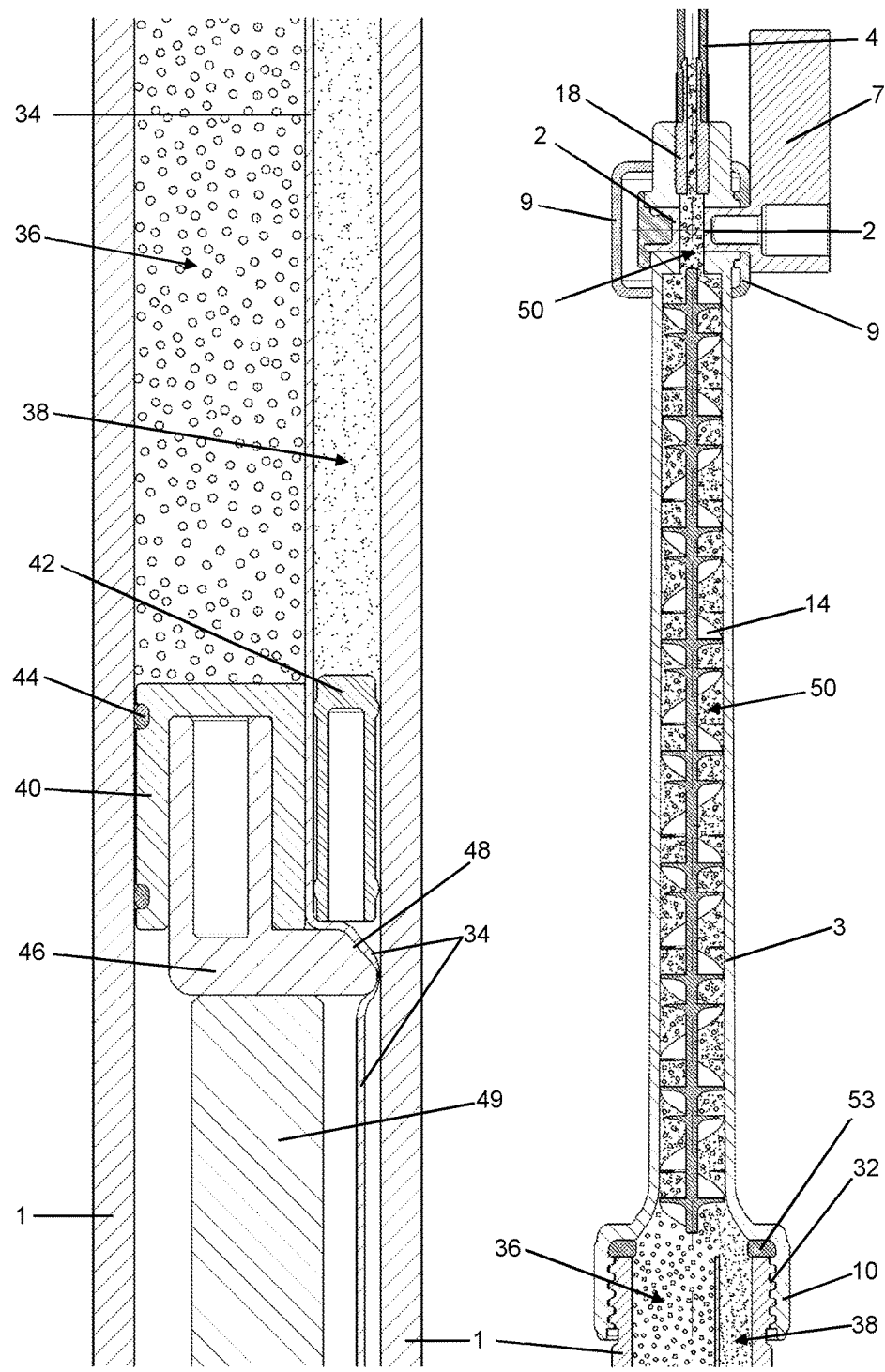
FIG. 9: shows two schematic cross-sectional views in longitudinal direction of the middle part of the cartridge (FIG. 9 left) and the middle part of the bone cement applicator (FIG. 9 right) of the first embodiment according to FIGS. 7 and 8 during the extrusion process.

FIG. 8 shows a schematic cross-sectional view in longitudinal direction of the rear side of the cartridge 1 of the first embodiment according to FIG. 7 before the start of the extrusion process. The content of the cartridges 1, 34 is also shown therein to allow for better illustration of the mixing process and the storage. FIG. 9 shows two schematic cross-sectional views in longitudinal direction of the middle part of the cartridge 1 of the first embodiment according to FIGS. 7 and 8 (FIG. 9 left) and of the middle part of the bone cement applicator (FIG. 9 right) during the extrusion process. The cartridge 1 according to FIGS. 7 and 8 is connected to a mixing tube 3 with a three-way valve 2 and a hose 4, as is depicted in FIGS. 1 to 6. FIG. 10 shows a schematic perspective magnified detail in the form of a cross-sectional view of the motion of the dispensing plungers and of the pressing device in the cartridge of the bone cement applicator according to the first embodiment according to FIGS. 7 to 9, whereby the content of the cartridges 1, 34 is not shown. FIG. 11 shows two schematic perspective sectional views of the front region of the cartridge 1 of the first embodiment of the bone cement applicator along with a closure, whereby the content of the cartridges 1, 34 is not shown.

Accordingly, the bone cement applicator for vertebroplasty shown to have the cartridge 1 according to FIGS. 7 to 11 comprises the external first cartridge 1 inside of which the internal second cartridge 34 is attached to the internal wall of the first cartridge 1 over the entire length of the first cartridge 1. Both cartridges 1, 34 are manufactured from the same material. The wall thickness of the internal second cartridge 34 corresponds to approximately one-fourth of the wall thickness of the external first cartridge 1. Except for the space taken up by the second cartridge 34, the internal space of the first cartridge 1 is filled with a first pasty starting component 36 of a PMMA bone cement. The internal space of the second cartridge 34 is filled with a second pasty starting component 38 of the two-component PMMA bone cement. The internal spaces of the cartridges 1, 34 are limited, on their rear sides (on the bottom in FIGS. 8 to 10), by a first dispensing plunger 40 in the first cartridge 1 and a second dispensing plunger 42 in the second cartridge 34, whereby the dispensing plungers 40, 42 close off the internal spaces of the cartridges 1, 34 towards the outside in fluid-tight manner. Accordingly, the dispensing plunger 40 of the first cartridge 1 comprises a lateral recess such that it can glide over the second cartridge 34, but also closes off tightly in this place. Matching the smaller internal space, the dispensing plunger 42 of the second cartridge 34 has a smaller diameter than the dispensing plunger 40 of the first cartridge 1.

The dispensing plunger 40 is sealed with respect to the internal wall of the external cartridge 1 by means of a seal 44. Two circumferential elevations are provided on the second dispensing plunger 42 as seals by means of which the second dispensing plunger 42 closes off against the internal walls of the second cartridge 34. By means of these seals 44, it can be made sure that the entire content of the two cartridges 1, 34, i.e. the two starting components 36, 38, are expelled completely and can thus be used for producing a PMMA bone cement mixture at the desired ratio. Since the wall of the second cartridge 34 is compressed by the second dispensing plunger 42 only after the second starting component 38 is expelled, the creases that are generated when the wall of the second cartridge 34 is being compressed do not retain residual amounts of the second starting component 38 and thus the mixing ratio in the cement dough is not being falsified.

The internal space of the second cartridge 34 is shaped to be cylindrical with a circular footprint. The internal space of the first cartridge 1 is also shaped to be cylindrical with a circular footprint, whereby the second cartridge 34 takes up a part of the internal space of the first cartridge 1 and thus effects a discontinuation of the circular symmetry of the internal space of the first cartridge 1. The dispensing plunger 40 of the first cartridge 1 comprises, on its rear side and/or bottom side (on the right in FIGS. 8 and 10, on the bottom left in FIG. 9), a depression into which a pressing device 46 is plugged. The pressing device 46 comprises, on its rear side, a clamping edge 48 that engages the space in the internal space of the first cartridge 1 that is occupied by the second cartridge 34, when the pressing device 46 is being propelled forward (towards the left in FIGS. 8 and 10, and towards the top in FIG. 9) inside the first cartridge 1. The clamping edge 48 comprises a chamfered surface that is inclined in the direction perpendicular to the cylinder axis of the second cartridge 34. The second cartridge 34 has a volume that corresponds to about one-twentieth of the volume of the first cartridge 1. Accordingly, the bone cement dough is mixed from the starting components 36, 38 at a mixing ratio of approximately 20 to 1.

Due to the cylindrical symmetry of the internal spaces of the cartridges 1, 34, the mixing ratio remains constant during the extrusion process.

The clamping edge 48 or the entire pressing device 46 consist of and/or are appropriately shaped from a material such that the pressing device 46 or at least the clamping edge 48 is harder or more solid than the wall of the second cartridge 34. Preferably, the clamping edge 48 and the entire pressing device 46 consist of a metal, in particular an aluminium alloy, or a solid plastic material that is at least harder, more solid and/or tougher than the material of the wall of the second internal cartridge 34.

The dispensing plungers 40, 42 are axially supported as in bearings such as to be mobile in longitudinal direction in the internal spaces of the cartridges 1, 34 in the direction of a cartridge head 31 of the cartridges 1, 34 (from right to left in FIGS. 8 and 10 and from bottom to top in FIG. 9). When the bone cement applicator is inserted into an extrusion device, the pressing device 46 and therefore the dispensing plungers 40, 42 are driven forward to the cartridge head 31 by a pestle 49 of the extrusion device and, in the process, the starting components 36, 38 are expelled and are mixed in the mixing tube 3 to form a bone cement 50. The first starting component 36 is contained in an internal space 51 of the first (external) cartridge 1, whereby the internal space 51 of the first cartridge 1 is limited by the internal wall of the first cartridge 1, by the external wall of the second (internal) cartridge 34, by the front side of the first dispensing plunger 40 and, if applicable, by a closure on the cartridge head 31. The second starting component 38 is contained in an internal space 52 of the second (internal) cartridge 34, whereby the internal space 52 of the second cartridge 34 is limited by the internal wall of the second cartridge 34, by the front side of the second dispensing plunger 42 and, if applicable, by a closure on the cartridge head 31. To make sure that no bone cement 50 is pushed outwards between the cartridge 1 and the mixing tube 3, a seal 53 is arranged in between. In the storage state of the bone cement applicator (see FIG. 11), a union nut 54 is screwed on in the region of the cartridge head 31 and is used to hold a rubber-elastic plate that limits the two openings of the cartridges 1, 34.

Two stoppers 56, 57 are plugged into the openings on the front side of the cartridges 1, 34 and close the openings and thus close the internal spaces of the cartridges 1, 34 on the front side in fluid-tight manner. The opening of the first cartridge 1 is placed appropriately such that it is aligned with and/or adjacent to the opening 24 of the second cartridge number 34.

The external thread 32 is provided on the outside of the front side of the first cartridge 1 as attachment element, onto which the union nut 54 can be and/or is screwed. For this purpose, the union nut 54 comprises a matching internal thread as a counter-attachment element. A socket with a connector 8 for attachment of the extrusion device is provided on the rear side of the bone cement applicator. The extrusion device supports the external first cartridge 1 and comprises the pestle 49 by means of which the pressing device 46 can be pushed in the direction of the cartridge head 31. Preferably, the extrusion device is driven manually.

Multiple static mixers 14 are arranged in the mixing tube 3 and mix the starting components 36, 38 with each other when these are being pressed through the mixing tube 3. This results in a well-mixed bone cement dough 50 that can be dispensed and/or applied by means of the application opening in a trocar that is connected to the Luer system adapter 5 or, just as well, by means of the application opening 6 on the tip of the Luer system adapter 5. The trocar can be part of the bone cement applicator according to the invention.

When the mixing tube 3 is attached to the first cartridge 1, the bone cement applicator is inserted into the extrusion device and is connected to the extrusion device by means of the connector 8. The pestle 49 of the extrusion device is driven into the bone cement applicator on the bottom side and thus presses onto the pressing device 46 on the bottom side. Since the first dispensing plunger 40 is connected to the pressing device 46, it is inserted into the first cartridge 1 by the pressing device 46 and, in the process, the first component 36 is pushed from the first cartridge 1 into the mixing tube 3. Simultaneously, the wall of the second cartridge 34 is pushed in the direction of the internal wall of the first cartridge 1 by the clamping edge 48. Due to the deformation of the wall of the second cartridge 34, the second dispensing plunger 42 is pushed in the direction of the cartridge head 31 and thus the second starting component 38 on the inside of the second cartridge 34 is pressed into the mixing tube 3. This situation is shown in FIG. 9.

Two depressions situated opposite from each other can be provided in the internal wall of the external first cartridge 1 as snap-in means (not shown). In this case, two matching counter-snap-in means (not shown) are provided in the first dispensing plunger 40, on the external jacket surface, and can engage the depressions and thus support the dispensing plunger 40 in the starting position that is suitable for storage of the starting components 36, 38 (see FIG. 8). The snap in-mechanism is detachable by pressing on the rear side of the dispensing plunger 40 and/or on the rear side of the pressing device 46 such that the first dispensing plunger 40, and thus the pressing device 46, can be moved in the direction of the cartridge head 31 when the snap-in resistance is overcome.

Using the inventive design of the first embodiment of the bone cement applicator, even very small amounts of the second starting component 38 can be admixed at the correct and/or desired mixing ratio. Conventional extrusion devices with a central pestle 49 can be used to mix and dispense the cement dough 50, since the wall of the second cartridge 34 is being pushed outwards in the direction of the first cartridge 1 and thus is not in the way of the motion of the pestle 49.

The external first cartridge 1 can be designed to be appropriately narrow, preferably, according to the invention, with an internal diameter of maximally 35 mm or particularly preferably with an internal diameter of maximally 20 mm, such that the viscous starting components 36, 38, in particular the viscous first starting component 36, can be pushed into the mixing tube 3 and through the static mixers 14 without the resistance of the viscous pastes 36, 38 being so large that these can no longer be expelled with conventional, manually-driven extrusion devices.

Using the three-way valve 2, the flow of the bone cement 50 can be interrupted without needing to release the pressure that is required for expelling the starting components 36, 38 from the two cartridges 1, 34 and for compressing the wall of the second internal cartridge 34. As a result, the pressing device 46 can be propelled again right after the three-way valve 2 is opened again. The excess of pressure in the hose 4 and, if applicable, in the trocar can be used up, at least in part, by the bone cement dough 50 flowing back through the three-way valve 2 into the collecting container 9, without any substantial amount of the bone cement dough 50 exiting to the front.

FIG. 12 shows an alternative of the first embodiment of the bone cement applicator according to the invention in the form of a magnified schematic cross-sectional view with two internal cartridges 34, 58 during the expulsion of the starting components 36, 38, 60.

The bone cement applicator (or the cartridge 1) according to FIG. 12 comprises an external first cartridge 1 that has an internal second cartridge 34 attached to an internal wall of the first cartridge 1 over the entire length of the first cartridge 1. Moreover, an internal third cartridge number 58 is attached on the opposite internal wall of the first cartridge 1 over the entire length of the first cartridge 1. All three cartridges 1, 34, 58 are manufactured from the same material. The wall thickness of the internal second cartridge 34 and of the internal third cartridge 58 corresponds to approximately one-fourth of the wall thickness of the external first cartridge 1. Except for the space taken up by the second cartridge 34 and the third cartridge 58, the internal space of the first cartridge 1 is filled with a first pasty starting component 36 of a multi-component PMMA bone cement. The internal space of the second cartridge 34 is filled with a second pasty starting component 38 of the multi-component PMMA bone cement. The internal space of the third cartridge 58 is filled with a third pasty starting component 60 of the multi-component PMMA bone cement. The internal spaces of the cartridges 1, 34, 58 are limited, on their rear sides (on the bottom in FIG. 12), by a first dispensing plunger 40 in the first cartridge 1, a second dispensing plunger 42 in the second cartridge 34, and a third dispensing plunger 62 in the third cartridge 58, whereby the dispensing plungers 40, 42, 62 close off the internal spaces of the cartridges 1, 34, 58 towards the outside in fluid-proof manner. Accordingly, the dispensing plunger 40 of the first cartridge 1 comprises two lateral recesses such that it can glide over the second cartridge 34 and the third cartridge 58. Matching the smaller internal space, the second dispensing plunger 42 of the second cartridge 34 and the third dispensing plunger 62 of the third cartridge 58 have a smaller diameter than the dispensing plunger 40 of the first cartridge 1.

The internal space of the second cartridge 34 and the internal space of the third cartridge 58 are shaped to be cylindrical with a circular footprint. The internal space of the first cartridge 1 is also shaped to be cylindrical with a circular footprint, whereby the second cartridge 34 and the third cartridge 58 take up a part of the internal space of the first cartridge 1 and thus effect a discontinuation of the circular symmetry of the internal space of the first cartridge 1. The dispensing plunger 40 of the first cartridge 1 comprises, on its rear side (on the bottom in FIG. 12), a depression into which a pressing device 46 is plugged. The pressing device 46 comprises, on its rear side, two clamping edges 48 and/or one clamping edge 48 that engage(s) the spaces in the internal space of the first cartridge 1 that are occupied by the second cartridge 34 and the third cartridge 58, when the pressing device 46 is being propelled forward (upwards in FIG. 12) inside the first cartridge 1. The clamping edges 48 each comprise an inclined surface that is inclined in the direction perpendicular to the cylinder axis of the second cartridge 34 and third cartridge 58. The second cartridge 34 and the third cartridge 58 have volumes of the same size and together have a volume that corresponds to approximately one-twentieth of [the volume of] the first cartridge 1. Accordingly, the cement dough is mixed from the three starting components 36, 38, 60 at a mixing ratio of approximately 40 to 1 to 1. Due to the cylindrical symmetry of the internal spaces of the cartridges 1, 34, 58, the mixing ratio remains constant during the extrusion process.

Instead of a third starting components 60, the second component 38 can also be contained both in the second cartridge 34 and in the third cartridge 58. By this means, a two-component bone cement is mixed at a mixing ratio of 20 to 1. The advantage as compared to the variant of the first embodiment shown in FIGS. 7 to 11 is that, due to the symmetrical design, no forces acting perpendicular to the cylinder axis and/or symmetry axis can be generated during the dispensation of the starting components 36, 38, due to which the pressing device 46 might get tilted and thus get impeded in its motion.

The clamping edge 48 or the entire pressing device 46 consist of one material and/or are appropriately shaped such that the pressing device 46 or at least the clamping edge 48 is harder or more solid than the wall of the second cartridge 34 and the wall of the third cartridge 58. Preferably, the clamping edge 48 and the entire pressing device 46 consist of a metal, in particular an aluminium alloy, or a solid plastic material that is at least harder, more solid and/or tougher than the material of the wall of the second internal cartridge 34 and of the third internal cartridge 58.

The dispensing plungers 40, 42, 62 are axially supported as in bearings such as to be mobile in longitudinal direction in the internal space of the cartridges 1, 34, 58 in the direction of a cartridge head of the cartridges 1, 34, 58 (from bottom to top in FIG. 12). An opening of the first cartridge 1, an opening of the second cartridge 34, and an opening of the third cartridge 58 are provided in the cartridge head (not shown in FIG. 12). In storage condition, a union nut is screwed on in the region of the cartridge head analogous to the first variant of the first embodiment and is used to support a rubber-elastic plate that limits the three openings.

An external thread is provided on the outside of the front side of the first cartridge 1 as attachment element, onto which the union nut can be screwed. A socket with a connector for attachment of an extrusion device (not shown) is provided on the rear side of the cartridge 1. The extrusion device supports the external first cartridge 1 and comprises a pestle by means of which the pressing device 46 can be pushed in the direction of the cartridge head. The extrusion device is driven manually.

For use of the bone cement applicator according to the second variant of the first embodiment according to FIG. 12, the cartridge 1 is integrated like in FIGS. 1 to 6 and is connected to the mixing tube 3. Then, the bone cement applicator is inserted into the extrusion device (not shown) and is connected to the extrusion device via the connector. The pestle of the extrusion device is driven into the bone cement applicator on the bottom side and thus presses onto the pressing device 46 on the bottom side. Since the first dispensing plunger 40 is connected to the pressing device 46, it is inserted into the first cartridge 1 by the pressing device 46 and, in the process, the first component 36 is pushed from the first cartridge 1 into the mixing tube 3. Simultaneously, the wall of the second cartridge 34 and the wall of the third cartridge 58 are pushed in the direction of the internal wall of the first cartridge 1 by the clamping edge 48 and the opposite clamping edge 48, respectively. Due to the deformation of the wall of the second cartridge 34, the second dispensing plunger 42 is pushed in the direction of the cartridge head 12 (upwards in FIG. 12) and thus the second starting component 38 on the inside of the second cartridge 34 is pressed into the mixing tube 3. Likewise, due to the deformation of the wall of the third cartridge 58, the third dispensing plunger 62 is being pushed in the direction of the cartridge head and thus the third starting component 60 on the inside of the third cartridge 58 is pressed into the mixing tube 3.

Two circumferential elevations are provided on the first dispensing plunger 40 as seals (not shown in FIG. 12), by means of which the dispensing plunger 40 closes off against the internal walls of the first cartridge 1. Likewise, two circumferential elevations are provided on the second dispensing plunger 42 as seals by means of which the second dispensing plunger 42 closes off against the internal walls of the second cartridge 34. Moreover, two circumferential elevations are provided on the third dispensing plunger 62 as seals by means of which the third dispensing plunger 62 closes off against the internal walls of the third cartridge 58. By means of these seals, it can be made sure that the entire content of the three cartridges 1, 34, 58, i.e. the three starting components 36, 38, 60, are expelled completely and can thus be used for producing a PMMA bone cement mixture at the desired ratio. Since the wall of the second cartridge 34 is compressed only after the second starting component 42 is expelled and the wall of the third cartridge 58 is compressed only after the third starting component 60 (or, alternatively, the second starting component 42) is expelled, the creases that are generated when the wall of the second cartridge 34 and the wall of the third cartridge 58 are being compressed do not retain residual amounts of the second starting component 38 and of the third starting component 60 and thus the mixing ratio in the cement dough is not being falsified.

Using the inventive design of the bone cement applicator according to the second variant of the first embodiment, even very small amounts of the second starting component 38 and of the third starting components 60 can be admixed at the correct and/or desired mixing ratio. Conventional extrusion devices with a central pestle can be used to mix and dispense the cement dough, since the walls of the second cartridge 34 and of the third cartridge 58 are being pushed outwards in the direction of the first cartridge 1 and thus are not in the way of the motion of the pestle.

The external first cartridge 1 can be designed to be appropriately narrow, preferably, according to the invention, with an internal diameter of maximally 35 mm or particularly preferably with an internal diameter of maximally 20 mm, such that the viscous starting components 36, 38, 60, in particular the viscous first starting component 36, can be pushed into the mixing tube 3 and through the static mixers 14 without the resistance of the viscous pastes 36, 38, 60 being so large that these can no longer be expelled with conventional, manually-driven extrusion devices.

Figure 13:
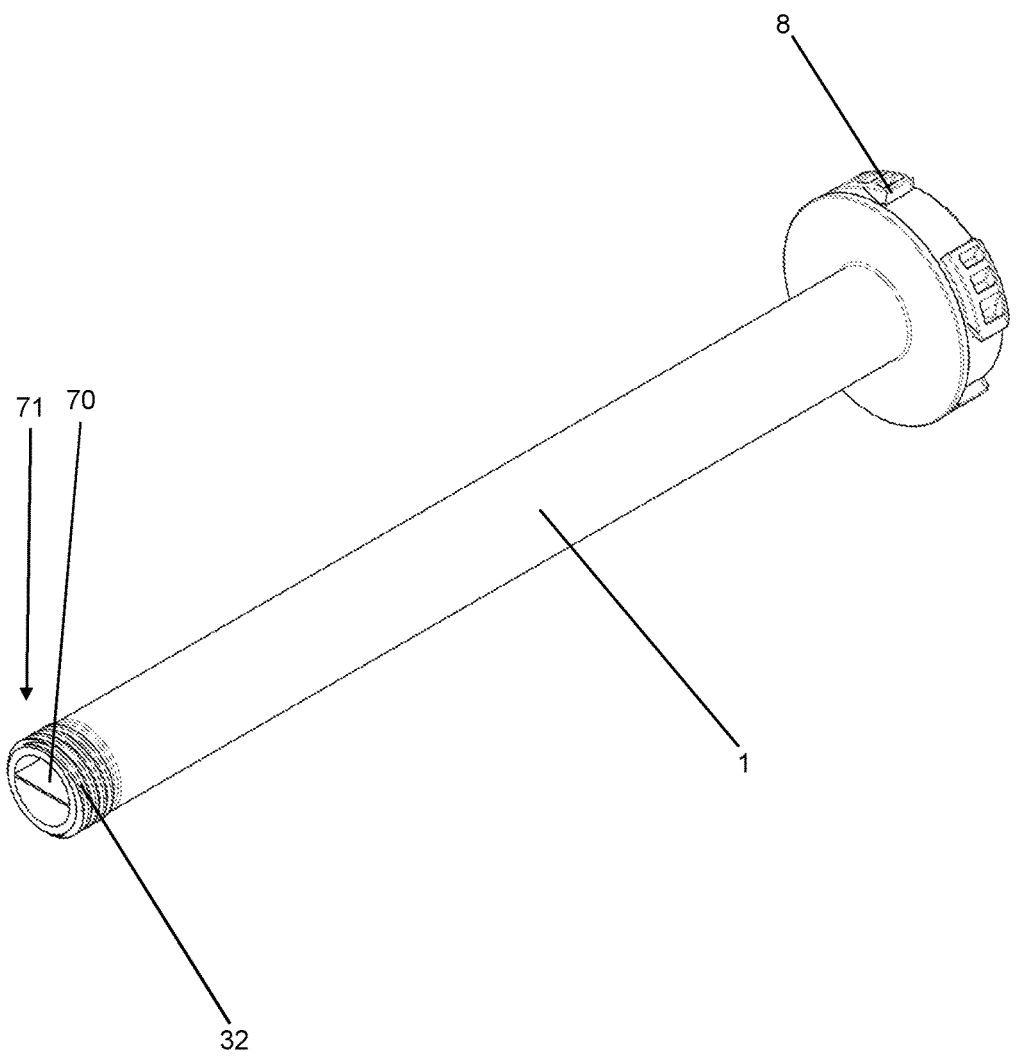
FIG. 13: shows a schematic perspective view of a cartridge having a separating wall for implementation of a second embodiment of a bone cement applicator according to the invention.

FIGS. 13 to 19 show a second embodiment of a bone cement applicator according to the invention, in which, as before, only the internal design of cartridge 1 differs from the first embodiment. In this context, FIG. 13 shows a schematic perspective view of a cartridge 1 having a separating wall 70 for implementation of the second embodiment of a bone cement applicator according to the invention. An external thread 32 is provided on the cartridge head 71 of the cartridge according to the second embodiment. Said cartridge 1 is well-suited for implementation of a second embodiment of a bone cement applicator according to the invention and, in the form shown, can be used as cartridge 1 in the bone cement applicator depicted in FIGS. 1 to 6. FIG. 13 shows a perspective view onto the open cartridge head 71. A closure can be screwed onto the external thread 32 in order to close the regions of the cartridge 1 that are subdivided by the separating wall 70 such that their internal spaces are completely closed.

Figure 14:
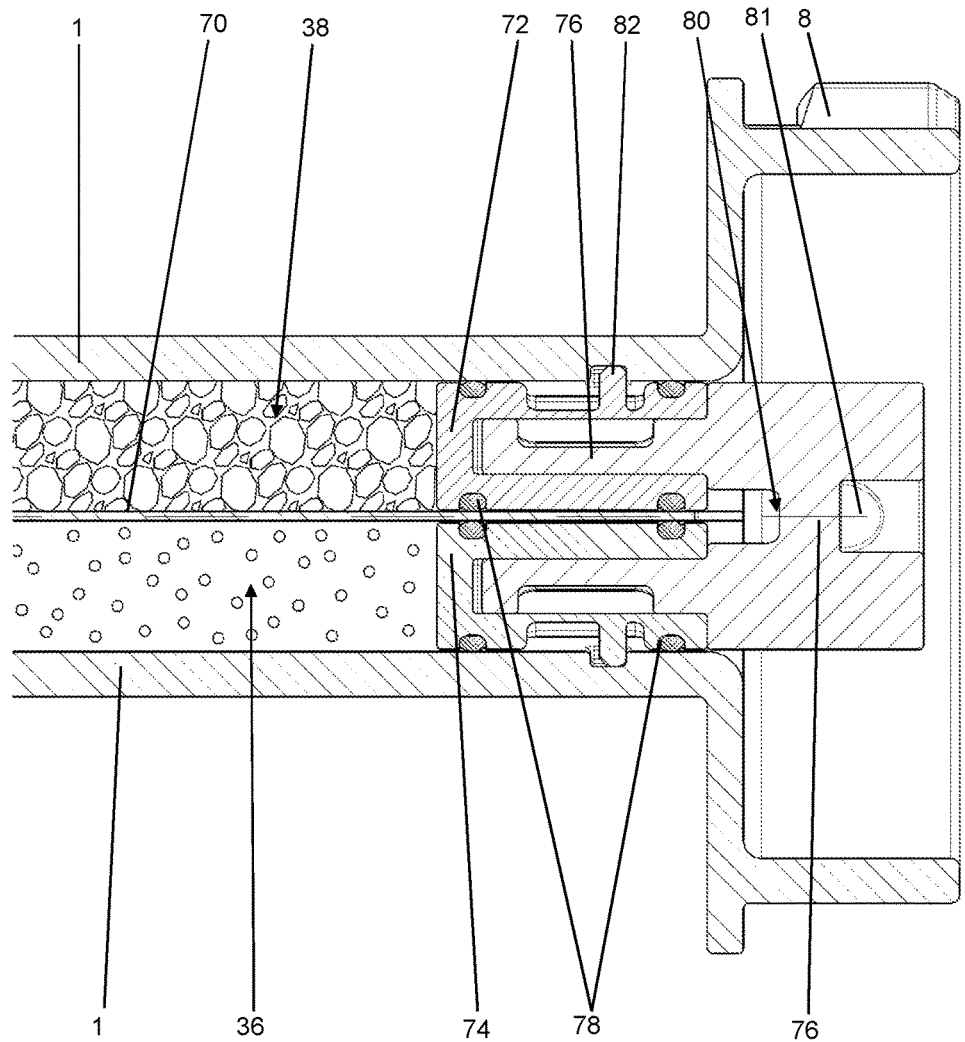
FIG. 14: shows a schematic cross-sectional view in longitudinal direction of the rear side of the cartridge of the second embodiment according to FIG. 13 before the start of the extrusion process.
Figure 15:
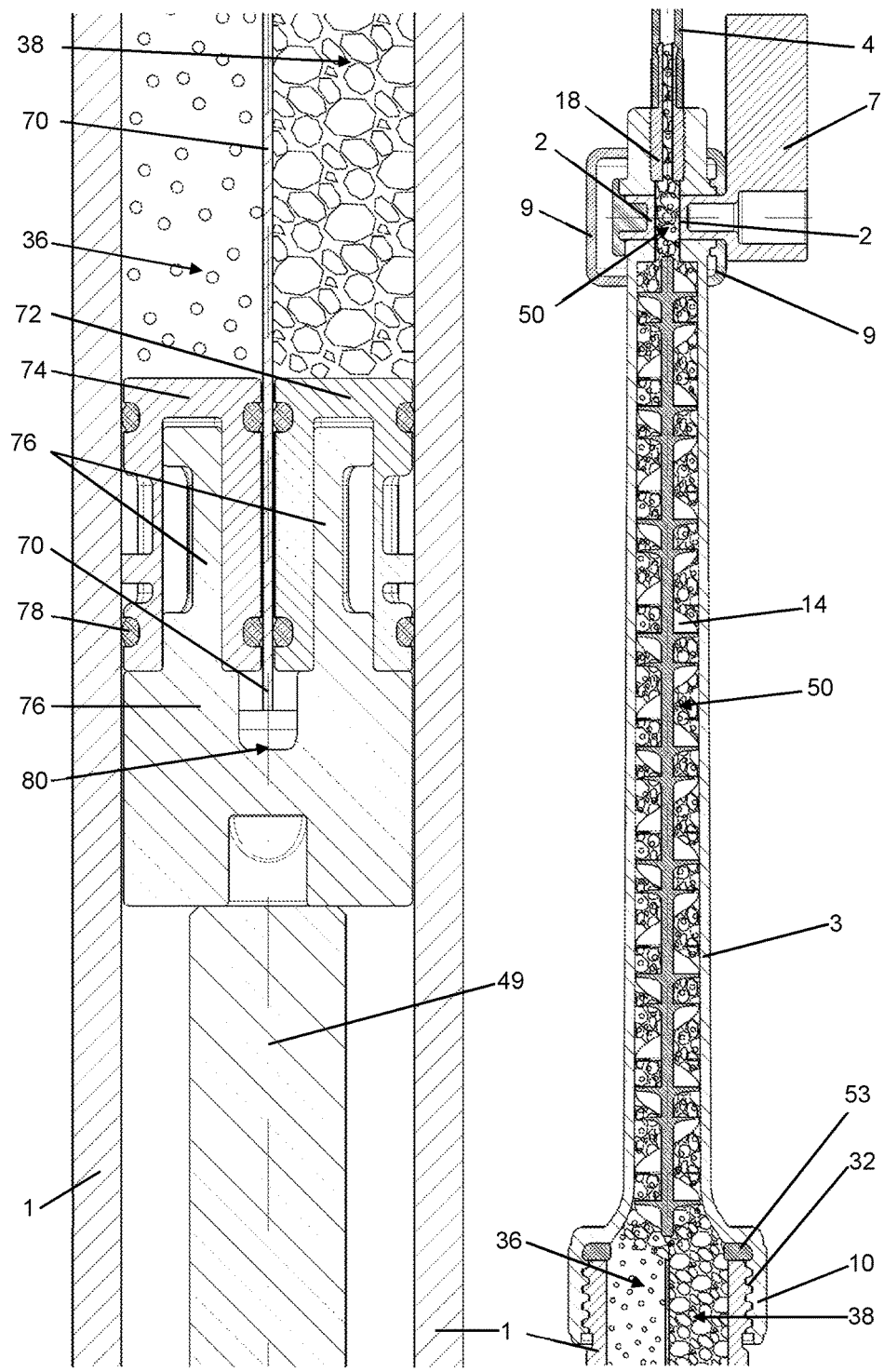
FIG. 15: shows two schematic cross-sectional views in longitudinal direction of the middle part of the cartridge (FIG. 15 left) and the middle part of the bone cement applicator (FIG. 15 right) of the second embodiment according to FIGS. 13 and 14 during the extrusion process.
Figure 16:
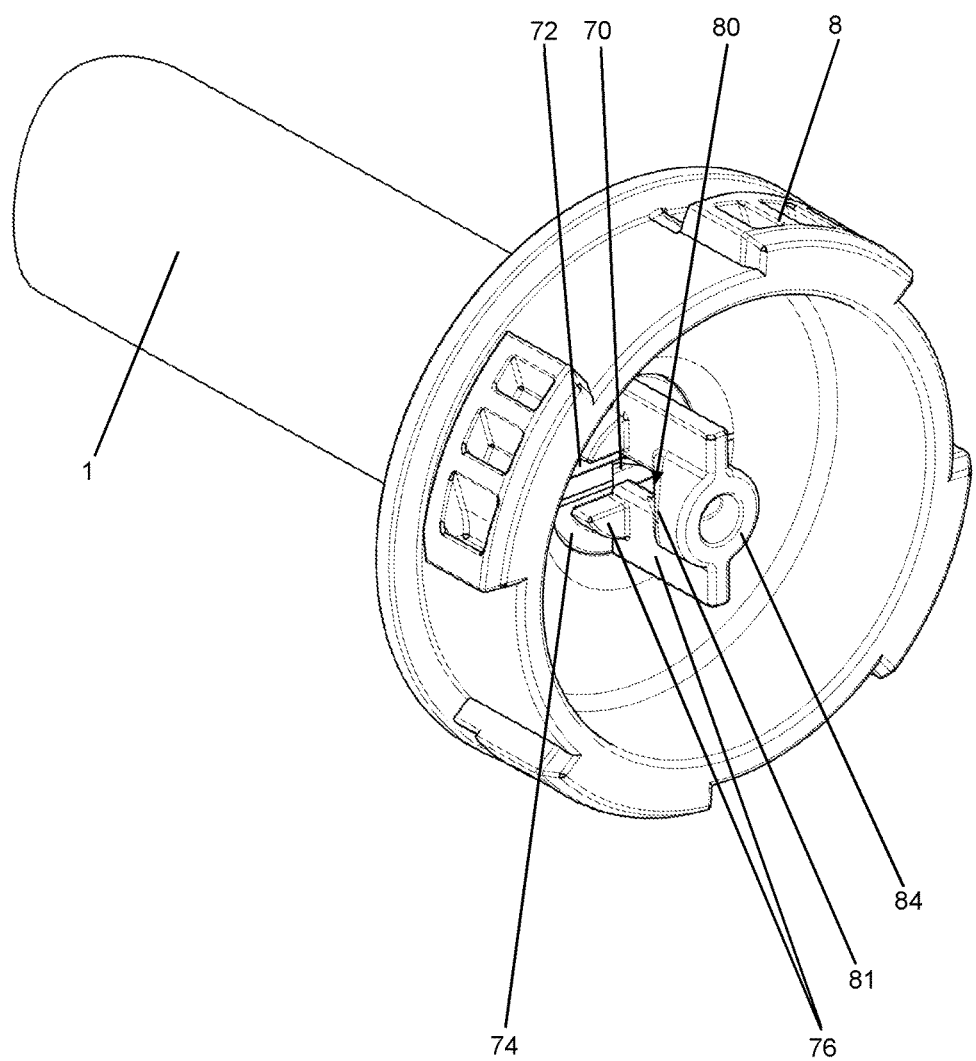
FIG. 16: shows a schematic perspective view of the rear side of the cartridge of the second embodiment of the bone cement applicator according to FIGS. 13 to 15.
Figure 17:
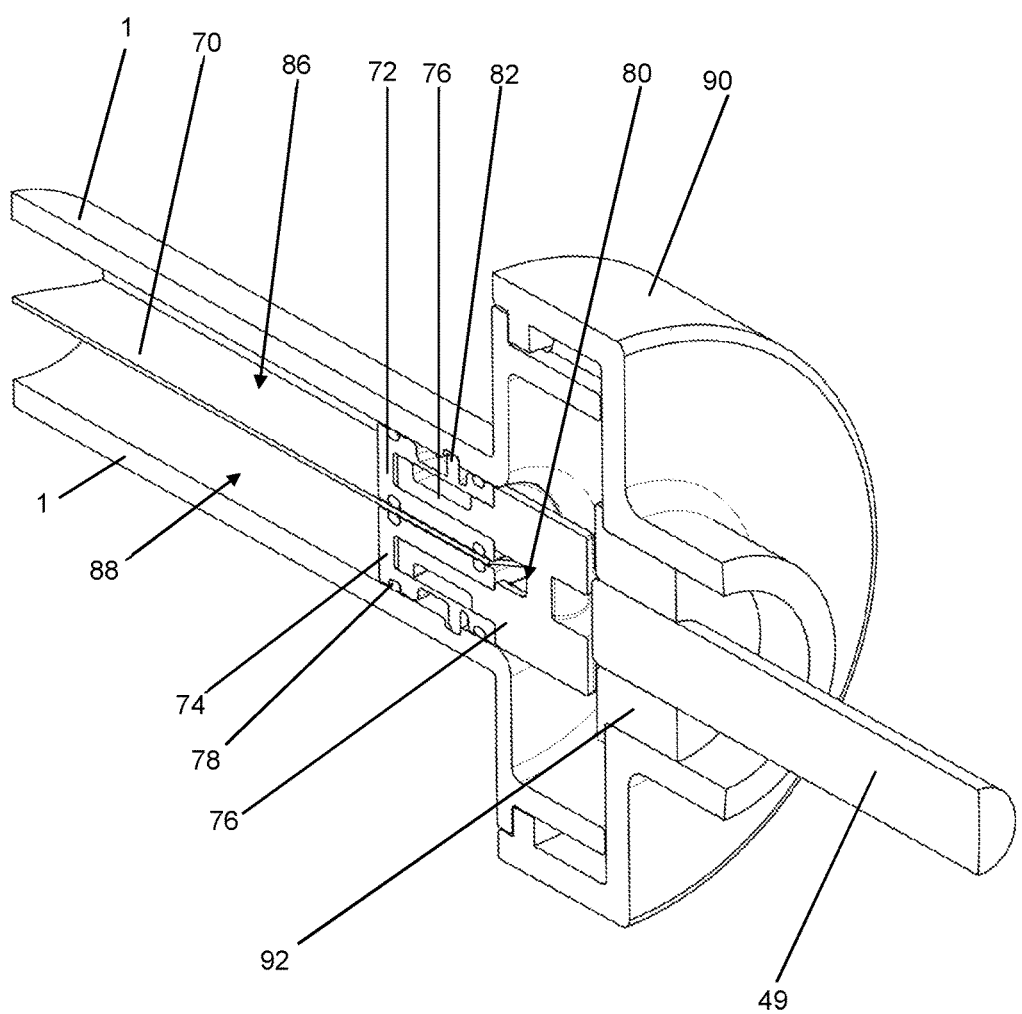
FIG. 17: shows a schematic perspective cross-sectional view of the rear side of the second embodiment of the bone cement applicator according to FIG. 16, inserted into an extrusion device.
Figure 18:
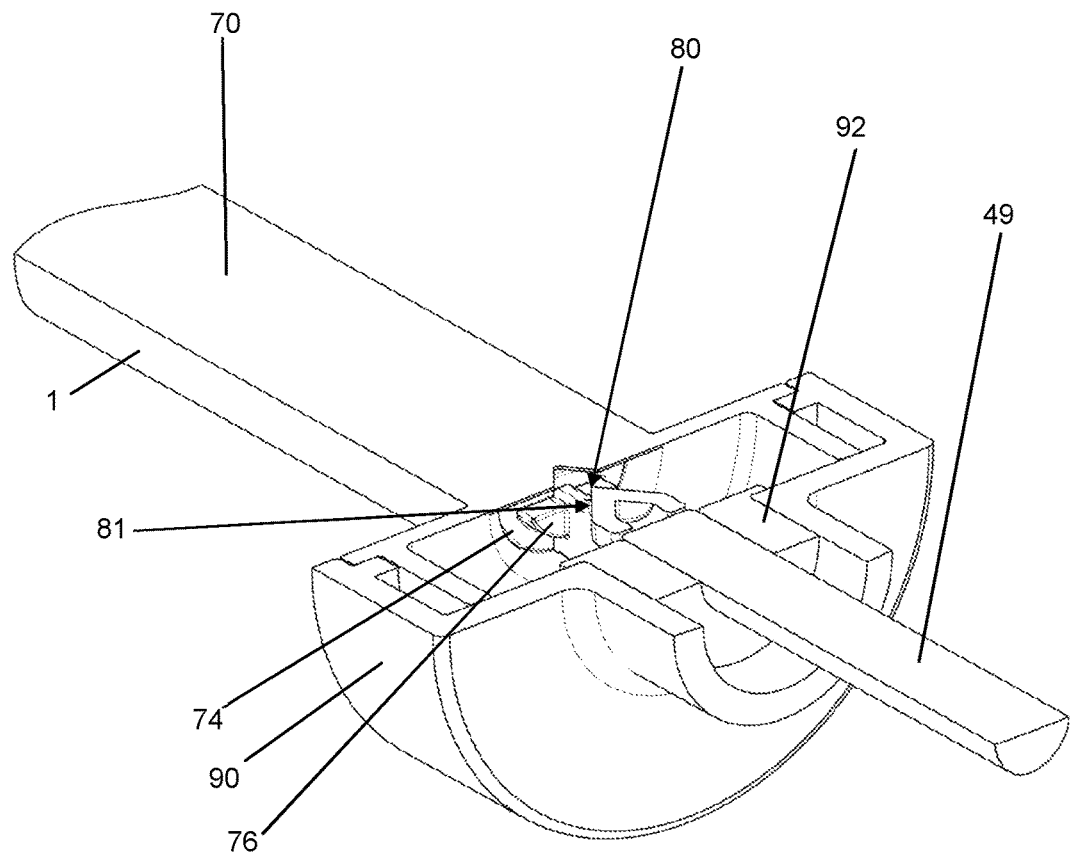
FIG. 18: shows a schematic perspective cross-sectional view of the rear side of the second embodiment of the bone cement applicator according to FIG. 16, inserted into an extrusion device, whereby the sectional plane is selected to be perpendicular to the one according to FIG. 17.
Figure 19:
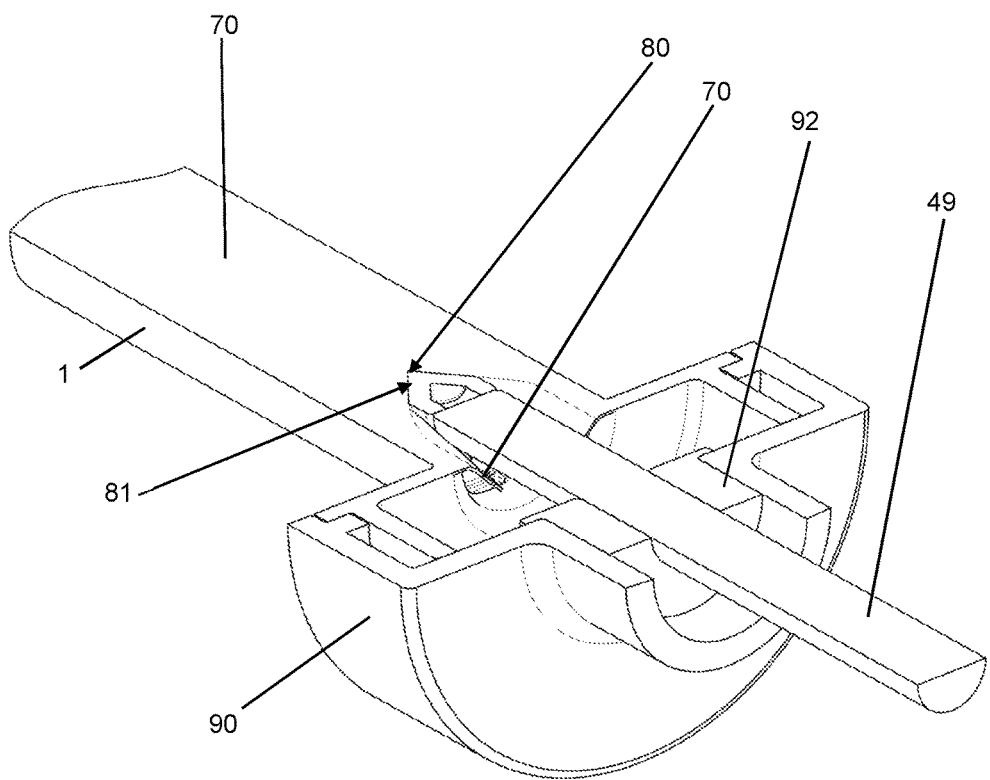
FIG. 19: shows a schematic perspective cross-sectional view of the rear side of the second embodiment of the bone cement applicator according to FIG. 16, inserted into the extrusion device, with the sectional plane according to FIG. 18, whereby the connecting means was driven forward by the pestle of the extrusion device in order to extrude the starting components of the bone cement.

FIG. 14 shows a schematic cross-sectional view in longitudinal direction of the rear side of the cartridge 1 of the second embodiment according to FIG. 13 before the start of the extrusion process, and FIG. 15 shows two schematic cross-sectional views in longitudinal direction of the middle part of the cartridge (FIG. 15 left) and of the middle part of the bone cement applicator (FIG. 15 right) of the second embodiment according to FIGS. 13 and 14 during the ongoing extrusion process. FIG. 16 shows a schematic perspective view of the rear side of the cartridge of the second embodiment of the bone cement applicator according to FIGS. 13 to 15, and FIG. 17 shows a schematic perspective cross-sectional view of the rear side of the second embodiment of the bone cement applicator according to FIG. 16 that is inserted in an extrusion device. Moreover, FIG. 18 shows a schematic perspective cross-sectional view of the rear side of the second embodiment of the bone cement applicator according to FIG. 16 that is inserted in an extrusion device, whereby the sectional plane is selected to be perpendicular to the one according to FIG. 17, and FIG. 19 shows a schematic perspective cross-sectional view of the rear side of the second embodiment of the bone cement applicator according to FIG. 16, that is inserted into the extrusion device, with the sectional plane according to FIG. 18.

The bone cement applicator according to the second embodiment comprises, as a central component, a cylindrical cartridge 1, in which a separating wall 70 connects two opposite internal sides of the internal wall of the cylindrical cartridge 1. The cartridge 1 and the separating wall 70 are designed as one part as a joint injection moulded part. The separating wall 70 subdivides the internal space of the cartridge 1 into two separate and fluid-tightly separated hollow spaces 86, 88 (see FIG. 17), in which the two pasty starting components 36, 38 of a PMMA bone cement 50 to be mixed are stored.

On the rear side (on the right in FIGS. 13 and 14), the hollow spaces 86, 88 are limited by two dispensing plungers 72, 74, whereby the dispensing plungers 72, 74 are axially supported as in bearings in the two hollow spaces 86, 88 such that they can be shifted. This context, FIG. 17 shows a detailed view in the form of a magnified schematic perspective partial cross-sectional view of the cartridge floor of the second embodiment of the bone cement applicator according to the invention. On the front side of the cartridge 1 that is situated opposite from the dispensing plungers 72, 74, the two hollow spaces 86, 88 are closed by a cartridge head 71 with a rubber-elastic plate, when the cartridge 1 is used for storage of the starting components 36, 38. For application of the bone cement 50, the two hollow spaces 86, 88 of the cartridge 1 are opened by opening the cartridge head 71 and the cartridge 1 is then connected to the mixing tube 3, the three-way valve 2, and the hose 4, such as is shown in FIGS. 1 to 6, whereby a trocar is being connected to the Luer system adapter 5. Subsequently, the bone cement applicator is inserted into an extrusion device by means of which the dispensing plungers 72, 74 can be pressed forward by hand in the direction of the mixing tube 3 in order to expel the starting components 36, 38 from the hollow spaces 86, 88 of the cartridge 1.

Two feedthroughs, each closed by a stopper (not shown), can be provided in the cartridge head 71. The two hollow spaces 86, 88 are accessible through the two feedthroughs, when the stoppers are not plugged into them and/or when the cartridge head 71 is open.

On the rear side of the cartridge 1 and/or on the floor side (on the right in FIGS. 13 and 14), a connector 8 with attachment elements is arranged on the cartridge 1. The cartridge 1 can be connected to the extrusion device and/or an applicator (not shown in FIGS. 13 and 14) by means of the connector 8 and the attachment elements. On the opposite front side (on the left in FIG. 1) of the cartridge 1, a closure (not shown) with a union nut (not shown) can be attached on the cartridge head 71 in the storage condition of the bone cement applicator in that an internal thread of the union nut is screwed onto an external thread 32 on the cartridge 1. In this case, a rubber-elastic plate seals the hollow spaces 86, 88 towards the front. The cartridge 1 has an external diameter of 27 mm, an internal diameter of 25 mm, and a length of approximately 18 cm.

The two dispensing plungers 72, 74 are connected to each other on their rear side by means of a connecting means 76. For this purpose, two cylinder-segment-shaped ends of the connecting means 76 facing in the direction of the cartridge head extend into fitting hollow spaces in the rear sides of the dispensing plungers 72, 74. The dispensing plunger 72, 74 are sealed on the outside against the internal wall of the cartridge 1 and against the separating wall 70 by means of two circumferential rubber seals 78 each. A front edge of the connecting means 76 pointing in the direction of the separating wall 70 is designed as a cutter with a blade 80 that widens in the direction of the rear side of the bone cement applicator via a wedge 81 or cone 81 and/or in wedge-shaped and partially cone-shaped manner. On the rear side of the wedge 81 and/or cone 81, the connecting means 76 is shaped to form a contact surface 84 for a pestle 49 of an extrusion device (not shown).

The dispensing plungers 72, 74 are connected to one detachable snap-in element 82 with matching counter snap-in elements (in the form of two depressions) each in the internal wall of the cartridge 1. The dispensing plungers 72, 74 can be pushed in the direction of the front side of the cartridge 1 (on the left in FIG. 1), i.e. in the direction of the cartridge head 7, by pressing from the rear side of the cartridge 1 (on the right in FIG. 1). The snap-in elements 82 can be easily detached by pressing on the floor side of the dispensing plungers 72, 74, when the cartridge head 71 is open or the stoppers are removed, and mainly serve to ensure that the dispensing plungers 72, 74 cannot be pushed out of the cartridge 1 on the floor side, when the starting components 36, 38 are filled into the internal space of the cartridge 1, and/or cannot be pushed in the direction of the cartridge floor (on the right in FIG. 1) beyond the desired position defined by the counter snap-in elements in the internal wall of the cartridge 1.

FIG. 14 shows a schematic perspective cross-sectional view through the inventive bone cement applicator according to the second embodiment, right before application of the PMMA bone cement. FIG. 15 shows the bone cement applicator according to the second embodiment while the two starting components 36, 38 are being expelled.

The starting components 36, 38 are mixed by pushing them through the mixing tube 3 and thus through the static mixer 14. This results in a well-mixed bone cement dough 50 that can be dispensed and/or applied by means of the application opening in a trocar that is connected to the Luer system adapter 5 or, just as well, by means of the application opening 6 on the tip of the Luer system adapter 5. The trocar can be part of the bone cement applicator according to the invention.

The mixing tube 3 comprises an internal thread that fits onto the external thread 32 of the cartridge 1 such that the mixing tube 3 can be stably and firmly connected to the cartridge 1. A sealing ring 53 is arranged between the mixing tube 3 and the front side of the cartridge 1 to prevent the starting components 36, 38 from leaking between the mixing tube 3 and the cartridge 1. A pressure-resistant and pressure-tight connection between the mixing tube 3 and the cartridge 1 is attained by means of the external thread 32, the internal thread, and the sealing ring 53.

The propulsion of the dispensing plungers 72, 74 is generated by means of an extrusion device that is being connected to the connector 8 and by means of which a pestle 49 and/or a push rod of the extrusion device is propellable in a forward direction by hand in the direction of the mixing tube 3. The pestle 49 then pushes onto the contact surface 84 such that, on the one hand, the dispensing plungers 72, 74 are propelled in the direction of the mixing tube 3 and, on the other hand, the blade 80 is driven into and cuts the separating wall 70, such as is depicted in FIG. 19. In this context, the pressure of the pestle 49 detaches the snap-in elements 82 and propels the dispensing plungers 72, 74 forward. The dispensing plungers 72, 74 close off tightly against the internal walls of the cartridge 1 and of the separating wall 70. As a result, the content of the hollow spaces 86, 88 of the cartridge 1, namely the two pasty starting components 36, 38 contained therein, are expellable forward into the mixing tube 3, where the starting components 36, 38 are mixed to form the cement dough 50.

Once the hollow spaces 86, 88 are opened, the cartridge 1 can be connected to the other main parts 2, 3, 4 of the bone cement applicator, and the bone cement applicator is being connected to the extrusion device by means of the connector 8 and/or by means of the attachment means.

The connecting means 76 is propelled forward in the direction of the mixing tube 3 by pressing onto the contact surface 84. These scenarios, together with the main parts of an extrusion device for propelling the connecting means, are shown in FIGS. 17 to 19. The snap-in means 82 detach from the depressions and the dispensing plungers 72, 74 are pushed forward in the hollow spaces 86, 88. In this context, the two starting components 36, 38 are pressed forward into the mixing tube 3, and are mixed therein. If the connecting means 76 are propelled further, not only are the dispensing plungers 72, 74 propelled forward further into the hollow spaces 86, 88 of the cartridge 1, but the blade 80 also engages the notch of the separating wall 70 and starts to cut open the separating wall in axial direction. Said scenario is depicted in FIGS. 15 and 17.

If the connecting means 76 is propelled forward even more, the wedge 81 or cone 81 arranged behind the blade 80 pushes apart the cut-open parts of the separating wall, which remain connected to the internal wall of the cartridge 1, and pushes them in the direction of the internal wall of the cartridge 1. Concurrently, the starting components 36, 38 are pushed further out of the hollow spaces 86, 88 into the mixing tube 3, and are mixed therein. Lastly, the ready-mixed cement dough 50 exits through the three-way valve 2, the hose 4, the Luer system adapter 5, the trocar (not shown) if applicable, and the dispensing opening 6, and can be applied at the desired site. Using the three-way valve 2, the flow of the bone cement 50 can be interrupted without needing to release the pressure that is required for expelling the starting components 36, 38 from the two hollow spaces 86, 88 and for cutting the separating wall 70. As a result, the connecting means 76 can be propelled again right after the three-way valve 2 is opened again. The excess of pressure in the hose 4 and, if applicable, in the trocar can be used up, at least in part, by the bone cement dough 50 flowing back through the three-way valve 2 into the collecting container 9, without any substantial amount of the bone cement dough 50 exiting to the front.

The connecting means 76 is shaped, roughly, like a yoke and comprises 2-fold rotational symmetry as well as a mirror plane for a plane of symmetry, whereby the 2-fold rotational symmetry axis extends in the mirror plane. In integrated condition, the 2-fold rotational symmetry axis coincides with the axis of the cartridge 1, i.e. with the cylinder axis of the cartridge 1.

The side of the connecting means 76 that faces the mixing tube 3 consists of two cylinder segments that are cut in a plane parallel to their cylinder axis, whereby two depressions are arranged on the jacket surface of the cylinder segments as counter snap-in mechanism for one snap-in means each in the dispensing plungers 72, 74. Accordingly, the two cylinder segments of the connecting means 76 snap-into the dispensing plungers 72, 74, when they are plugged into the openings dedicated for this purpose on the rear side of the dispensing plungers 72, 74 that is situated opposite from the mixing tube 3.

The two cylinder segments are connected to each other by means of a plate, in the middle of which is arranged a central perpendicular cylinder with a circular footprint 84 that forms the contact surface 84 for a pestle 49 (see FIGS. 15 and 17 to 19) of an extrusion device. On the opposite side of the central cylinder, the footprint is inclined and forms the wedge 81 and/or cone 81. The blade 80 that bridges the gap between the two cylinder segments is arranged on the tip of the wedge 81 or cone 81. The two cylinder segments are maintained at a fixed distance with respect to each other by means of the plate and the central perpendicular cylinder. The distance is selected appropriately such that the two dispensing plungers 72, 74, plugged onto the cylinder segments of the connecting means 76, are maintained at a distance from each other that is somewhat smaller or at most the same as the thickness of the separating wall 70, i.e. for example 1 mm. The blade 80 can be an insert made of a hard metal or a hard plastic material or the entire connecting means 76 can be made from a material of this type that needs to be hard enough to be able to cut-open the separating wall 70, when the connecting means 70 is propelled in the direction of the mixing tube 3 in the cartridge 1.

FIGS. 17, 18, and 19 show only a connector 90 for connection to the attachment means of the bone cement applicator, a pestle 49, and a bearing 92 for the pestle 49 of the extrusion device. These parts and the remaining components of the extrusion device correspond to those of conventional manually or electrically or pneumatically driven extrusion devices. The extrusion device has a compartment for accommodation of the bone cement applicator, whereby the bone cement applicator is supported stably at least on the front side in the region of the thread 32 and on the rear side on connector 8. The connector 90 of the extrusion device is to be connected to the connector 8 of the bone cement applicator. The pestle 49 acting as push rod 49 can be moved and/or driven against the connector 90 of the extrusion device in the direction through the connector 90 and/or in the direction into the cartridge 1, since it is supported in the bearing 92 such as to be mobile along its longitudinal axis. In this context, the tip of the pestle 49 pushes onto the contact surface 84 of the connecting element 76. By this means, the connecting element 76 and the two dispensing plungers 72, 74 are propelled in the direction of the mixing tube 3.

Spreading the two cut-open parts of the separating wall 70 by means of the wedge 81 or cone 81 of the connecting means 76 causes the parts of the separating wall 70 to be pushed in the direction of the internal wall of the cylindrical internal space of the cartridge 1 and away from the pestle 49 that moves on the inside the cartridge 1. As a result, the 2 cut-open parts of the separating wall 70 cannot impede any further motion of the pestle 49. Despite the high viscosity of the pasty starting components 36, 38, despite the flow resistance caused by the static mixer 14, the long hose 4, and, if applicable, the trocar (not shown), and despite the force and/or energy expenditure required for cutting the separating wall 70 by the blade 80, this results in the resistance to the motion of the pestle 49 not getting so large that the cartridge 1 can no longer be extruded with conventional and manually-driven extrusion devices.

Cartridge 1 and connector 8 preferably have a one-part design in all embodiments and preferably consists of plastic material. Except for the seals 44, 53, 78, all parts of bone cement applicators according to the invention can be manufactured from plastic materials by injection moulding. The seals 44, 53, 78 preferably consists of rubber. The clamping edge 48 and/or the blade 80 preferably consists of a metal, a ceramic material, a metallic alloy or a particularly hard plastic material. The sleeves 12 and the inserts 18 as well as, if applicable, the trocar preferably also consist of a metallic material. In theory, the other parts of the bone cement applicator can also be manufactured from metallic materials. It is preferred to use pasty starting components of a PMMA bone cement as starting components.

The features of the invention disclosed in the preceding description and in the claims, figures, and exemplary embodiments, can be essential for the implementation of the various embodiments of the invention both alone and in any combination.

LIST OF REFERENCE NUMBERS

1 Cartridge
2 Three-way valve
3 Mixing tube
4 Hose
5 Luer system adapter
6 Application opening
7 T-handle
8 Connector
9 Collecting container
10 Union nut
12 Sleeve
14 Static mixer
16 Valve seat
18 Insert
19 Passage
20 Feed-through
22 Stopper
24 External sleeve
26 Internal thread
28 Internal part
30 Cone
31 Cartridge head
32 External thread
34 Internal cartridge
36 First starting component
38 Second starting component
40 First dispensing plunger
42 Second dispensing plunger
44 Seal
46 Pressing device
48 Clamping edge
49 Pestle/push rod
50 Bone cement dough
51 Internal space of the first cartridge
52 Internal space of the second cartridge
53 Seal
54 Union nut
56 Stopper
57 Stopper
58 Internal cartridge
60 Third starting component
62 Third dispensing plunger
70 Separating wall
71 Cartridge head
72 Dispensing plunger
74 Dispensing plunger
76 Connecting means
78 Seal
80 Blade
81 Wedge/cone
82 Snap-in means
84 Contact surface
86 Hollow space
88 Hollow space
90 Connector
92 Bearing

The invention claimed is:

1. A bone cement applicator comprising:
   at least one tubular cartridge with an internal space, wherein the internal space is configured to contain starting components of a bone cement;
   at least one dispensing plunger configured for expelling the starting components from the at least one cartridge through an opening of the at least one cartridge, wherein the at least one dispensing plunger is mobile in longitudinal direction on the inside of the at least one cartridge;
   a hose;
   an application opening through which the bone cement dough is applicable;
   a three-way valve being operable from outside and being arranged in the hose or on a side of the hose facing the at least one cartridge, wherein the three-way valve is in fluid connection with the opening of the at least one cartridge; and
   a collecting container arranged on the three-way valve for accommodation of bone cement dough;
   wherein the three-way valve is appropriately designed and is appropriately arranged in the bone cement applicator such that it,
   being in a first position, provides a fluid connection between the application opening and the opening of the at least one cartridge and closes a feed-through to the collecting container and,
   being in a second position, provides a fluid connection between the application opening and the collecting container and closes a passage to the opening of the at least one cartridge.

2. The bone cement applicator according to claim 1, further comprising:
   a mixer is arranged between the opening of the at least one cartridge and the hose or between the opening of the at least one cartridge and the three-way valve, wherein the three-way valve is arranged between the mixer and the hose, wherein the three-way valve, being in the first position, provides a fluid connection between the application opening and the mixer and, being in the second position, closes the passage to the mixer.

3. The bone cement applicator according to claim 1, wherein the bone cement applicator is operable by means of a manually operated extrusion device and in that the at least one dispensing plunger is movable in the at least one cartridge by manual force, wherein the cross-section of the internal space of the one cartridge is maximally 3.5 cm$^2$ or the cross-section of all internal spaces of the cartridges taken together is maximally 3.5 cm$^2$ and/or that the propulsion area of the at least one dispensing plunger is maximally 3.5 cm$^2$.

4. The bone cement applicator according to claim 1, wherein at least part of the hose is flexible and/or the application opening is arranged in a connection with an internal thread, in a Luer system adapter, or in a trocar.

5. The bone cement applicator according to claim 1, wherein the collecting container is impermeable for the bone cement dough towards the outside, the collecting container is fluid-tight or fluid-tight and gas-tight, and/or the collecting container has a volume that is at least as large as half the volume of the hose.

6. The bone cement applicator according to claim 1, wherein the at least one cartridge comprises, on its rear side, an attachment element for attachment of an extrusion device.

7. The bone cement applicator according to claim 1, further comprising:
   a first tubular cartridge with a first cylindrical internal space, wherein a first starting component of a bone cement is contained in the internal space;
   a first dispensing plunger that is arranged in the first internal space of the first cartridge such as to be axially mobile and that is provided for expelling the first starting component from the first cartridge through an opening in a cartridge head of the first cartridge that is situated opposite from the first dispensing plunger; and
   a second tubular cartridge that is arranged inside the first tubular cartridge, wherein the second cartridge contains a second starting component of the bone cement and has a second dispensing plunger arranged in it, wherein the second dispensing plunger is usable to expel the second starting component from the second cartridge through an opposite opening of the second cartridge in the region of the cartridge head of the first cartridge,
   wherein a pressing device is arranged in the internal space of the first cartridge behind the first dispensing plunger and the second dispensing plunger, as seen from the cartridge head, the pressing device comprising a clamping edge for compressing the second cartridge and being propellable axially, whereby the pressing device is propellable appropriately in the direction of the cartridge head such that the second cartridge is being progressively compressed axially during the motion of the pressing device thereby propelling the first dispensing plunger and the second dispensing plunger in the direction of the cartridge head.

8. The bone cement applicator according to claim 7, wherein the external wall of the second cartridge touches against the internal wall of the first cartridge and is attached to the internal wall of the first cartridge.

9. The bone cement applicator according to claim 7, wherein the first dispensing plunger and the second dispensing plunger are propelled parallel with respect to each other during the propulsion of the pressing device.

10. The bone cement applicator according to claim 7, wherein the clamping edge is inclined at an angle of at least 40° perpendicular to the longitudinal axis in the direction of the internal wall of the first cartridge.

11. The bone cement applicator according to claim 7, wherein a gap is provided between the pressing device and the internal wall of the first cartridge in the region of the second cartridge, whereby the gap is as wide as or wider than the thickness of the wall of the second cartridge.

12. The bone cement applicator according to claim 7, wherein the clamping edge, by squeezing the second cartridge, presses the thus deformed wall of the second cartridge against the underside of the second dispensing plunger and thus pushes the second dispensing plunger in the direction of the cartridge head while the pressing device is being propelled in the direction of the cartridge head.

13. The bone cement applicator according to claim 7, further comprising:
   a third tubular cartridge arranged inside the first tubular cartridge, wherein the external wall of the third cartridge touches against the internal wall of the first cartridge and is attached to the internal wall of the first cartridge, whereby the third cartridge contains the second starting component or a third starting component of the multicomponent bone cement and has a third dispensing plunger arranged in it, wherein the second starting component or the third starting component is expellable from the third cartridge, by means of the third dispensing plunger, through an opposite opening in the third cartridge in the region of the cartridge head of the first cartridge, wherein the pressing device is arranged behind the third dispensing plunger as seen from the cartridge head and the pressing device comprises a clamping edge for compressing the third cartridge, wherein the pressing device is propellable appropriately in the direction of the cartridge head such that the third cartridge is progressively compressed axially while the pressing device moves and thus the first dispensing plunger, the second dispensing plunger, and the third dispensing plunger are being propelled in the direction of the cartridge head.

14. The bone cement applicator according to claim 1, further comprising:
   a tubular cartridge, wherein the internal space of the cartridge is cylindrical;
   a cartridge head that limits an end of the tubular cartridge;
   a separating wall in an axial arrangement in the cylindrical internal space of the cartridge, whereby the separating wall is connected to the jacket surface of the cylindrical internal space of the cartridge, and wherein the separating wall subdivides the cylindrical internal space of the cartridge, which is limited by the cartridge head, into two spatially separated hollow spaces, whereby the first hollow space contains a first pasty starting component of the bone cement, and the separate second hollow space contains a second pasty starting component of the bone cement; and
      two dispensing plungers that are arranged in the two hollow spaces of the cartridge such as to be axially displaceable, wherein the dispensing plungers close off the two hollow spaces on the side of the hollow spaces opposite from the cartridge head,
      wherein the dispensing plungers are connected to each other on the rear side opposite from the cartridge head by means of a connecting means, wherein a wedge or cone with a blade on the front side of the wedge or cone facing the cartridge head is arranged on the connecting means such that, upon propulsion of the dispensing plungers in the hollow spaces in the direction of the cartridge head, the blade cuts open the separating wall and the wedge or cone pushes the cut-open parts of the separating wall in the direction of the internal wall of the cartridge.

15. The bone cement applicator according to claim 14, wherein the dispensing plungers are situated at an appropriate distance from each other by means of the connecting means such that the gap between the dispensing plungers is smaller than or equal to the thickness of the separating wall.

16. A method for application of a pasty multicomponent polymethylmethacrylate bone cement dough, the method comprising:
   a) providing a bone cement applicator, the bone cement applicator comprising:
      at least one tubular cartridge with an internal space, wherein the internal space is configured to contain starting components of a bone cement;
      at least one dispensing plunger configured for expelling the starting components from the at least one cartridge through an opening of the at least one cartridge, wherein the at least one dispensing plunger is mobile in longitudinal direction on the inside of the at least one cartridge;
      a hose;
      an application opening through which the bone cement dough is applicable;
      a three-way valve being operable from outside and being arranged in the hose or on a side of the hose facing the at least one cartridge, wherein the three-way valve is in fluid connection with the opening of the at least one cartridge; and
      a collecting container arranged on the three-way valve for accommodation of bone cement dough;
      wherein the three-way valve is appropriately designed and is appropriately arranged in the bone cement applicator such that it,
      being in a first position, provides a fluid connection between the application opening and the opening of the at least one cartridge and closes a feed-through to the collecting container, and,
      being in a second position, provides a fluid connection between the application opening and the collecting container and closes a passage to the opening of the at least one cartridge;
   b) inserting the bone cement applicator into an extrusion device, wherein the extrusion device comprises an axially propellable pestle for propulsion of the at least one dispensing plunger and/or of the pressing device or of the connecting means in the internal space of the at least one cartridge in the direction of the opening of the at least one cartridge;
   c) moving the three-way valve to the first position or the three-way valve being in the first position and extruding the starting components by means of the extrusion device by axial propulsion of a pestle of the extrusion device, whereby the pestle pushes the at least one dispensing plunger in the direction of the opening, by means of which the starting components are mixed to form the bone cement and the bone cement dough is pushed through the hose and out of the application opening; and
   d) moving the three-way valve to the second position, wherein the three-way valve, in the second position of the three-way valve, stops the flow of the starting components out of the at least one cartridge into the hose and part of the bone cement dough that is pressurised between the application opening and the three-way valve is pressed through the three-way valve into the collecting container.

17. The method according to claim 16, wherein the three-way valve is moved to the first position again in a step e) after step d) and, by this means, the bone cement dough is guided again through the three-way valve to the application opening, whereby it is preferred for steps c), d), and e) to be repeated once or multiple times in the order given.

18. The method according to claim 16, wherein, during the extrusion of the starting components in step b), the pressing device is propelled by the pestle in the direction of a mixing tube, the first dispensing plunger simultaneously being pushed in the direction of the mixing tube by the pressing device, the clamping edge of the pressing device pressing the wall of the second cartridge to the internal wall of the first cartridge, the deformed wall of the second cartridge simultaneously pushing the second dispensing plunger in the second cartridge in the direction of the mixing tube, by means of which the starting components of the bone cement of both cartridges are pushed into the mixing tube, wherein the starting components are mixed in the mixing tube to form a pasty cement dough, and the mixed cement dough flows out of an application opening.

19. The method according to claim 16, wherein, during the extrusion of the starting components in step b), the extrusion of the pasty starting components by means of the extrusion device takes place by axial propulsion of the dispensing plungers with the pestle, whereby the starting components are pushed into the hose, whereby, synchronous with the motion of the dispensing plungers, the separating wall is cut by the blade in the longitudinal direction of the cartridge and the wedge or cone pushes the two cut-open parts of the separating wall in the direction of the internal wall of the cartridge at least sufficiently far outwards such that a further motion of the pestle of the extrusion device is not prevented or impeded by parts of the cut-open separating wall.

* * * * *